United States Patent [19]
Gustafson et al.

[11] Patent Number: 6,140,361
[45] Date of Patent: Oct. 31, 2000

[54] USE OF 2-DEOXYSTREPTAMINE AS A MOLECULAR SCAFFOLD FOR THE PREPARATION OF FUNCTIONALLY AND SPATIALLY DIVERSE MOLECULES AND PHARMACEUTICAL COMPOSITIONS THEREOF

[75] Inventors: Gary R. Gustafson, Bedford; David G. Powers, Maynard; Mark A. Wuonola, Waltham, all of Mass.

[73] Assignee: Scriptgen Pharmaceuticals, Inc., Waltham, Mass.

[21] Appl. No.: 09/273,964

[22] Filed: Mar. 22, 1999

Related U.S. Application Data

[62] Division of application No. 08/709,343, Sep. 6, 1996, Pat. No. 5,942,547.
[60] Provisional application No. 60/003,458, Sep. 8, 1995.

[51] Int. Cl.[7] .......................... A61K 31/133; A61K 31/16; C07C 217/52
[52] U.S. Cl. .......................... 514/488; 514/548; 514/579; 514/616; 560/115; 560/251; 564/153; 564/158; 564/159; 564/461
[58] Field of Search .................................... 560/119, 251; 564/153, 158, 159, 461; 514/488, 548, 579, 616

[56] References Cited

U.S. PATENT DOCUMENTS

| | | | |
|---|---|---|---|
| 3,828,021 | 8/1974 | Beattie et al. | 260/210 |
| 3,872,080 | 3/1975 | Daniels | 260/210 |
| 4,218,561 | 8/1980 | Paulsen et al. | 536/17 |
| 4,396,609 | 8/1983 | Daum et al. | 424/180 |
| 5,288,514 | 2/1994 | Ellman | 427/2 |
| 5,496,938 | 3/1996 | Gold et al. | 536/22.1 |
| 5,534,408 | 7/1996 | Green et al. | 435/5 |
| 5,565,324 | 10/1996 | Still et al. | 435/6 |

FOREIGN PATENT DOCUMENTS

WO 94/09792  5/1994  WIPO .

OTHER PUBLICATIONS

Hanessian et al., Can. J. Chem., vol. 56, p.1482–1491, 1978.
Goda et al., Chemical Abstracts, vol. 117, abstract 151254, 19992.
Georgiadis et al., Chemical Abstracts, vol. 116, abstract 42009, 19992.
Hichens et al., Chemical Abstracts, vol. 80, abstract 13580, 1974.
Kawaguchi et al. Chemical Abstracts, vol. 78, abstract 84748, 1973.
A. Canas–Rodriguez et al., Carbohydrate Research, 68:43–53, 1979.
R.C. Pandey et al., J. of Chromatography, 170:498–501, 1979.
M.L. Zapp et al., Cell, 74:969–978, 1993.
Tamura et al, CA, 109:231413, 1988.
E. Voss et al, CA, 95:25529d, 1981.
A.H. Khan et al, CA, 110:113298, 1988.
D.M.Barends et al, CA, 96: 14880, 1981.
S. Hanessian et al, CA, 89:215683, 1978.
A.K. Mallams, CA, 81:13755, 1974.
S. Umezawa et al, CA, 70: 58219q, 1968.
S. Umezawa et al, CA, 62:2819h, 1965.

*Primary Examiner*—Richard L. Raymond
*Attorney, Agent, or Firm*—Darby & Darby

[57] ABSTRACT

2-Deoxystreptamine is an aminocyclitol whose structural stability and abundant functionality make it an attractive scaffold for the combinatorial generation of small molecules. The ability to selectively functionalize the various positions of 2-deoxystreptamine with an almost infinite number of different groups ensures that the libraries so generated will be both spatially and functionally diverse. These compounds can then be screened for biological activity to afford lead compounds for pharmaceutical programs. Additionally, biological ligand mimics based on 2-deoxystreptamine can be readily appended, either directly or through a tether, to solid surfaces or incorporated covalently into gels to afford novel materials useful in separation science.

8 Claims, 6 Drawing Sheets

USE OF 2-DEOXYSTREPTAMINE AS A MOLECULAR SCAFFOLD FOR THE PREPARATION OF FUNCTIONALLY AND SPATIALLY DIVERSE MOLECULES AND PHARMACEUTICAL COMPOSITIONS THEREOF

This is a division of application Ser. No. 08/709,343, filed Sep. 6, 1996, now U.S. Pat. No. 5,942,547, which claims priority under 35 U.S.C. § 119 provisional application Ser. No. 60/003,458, filed Sep. 8, 1995. Both prior appplications are hereby incorporated by reference in their entirety.

FIELD OF THE INVENTION

The present invention relates to the preparation of small-molecule therapeutics based on 2-deoxystreptamine. The invention includes the preparation of broad "universal Libraries" of compounds that are useful for lead/hit discovery, especially in the field of RNA targeted drugs. Also disclosed are "directed libraries" that are useful for developing structure-activity relationships in a lead series, in particular, for a given transcriptional (RNA) target. These molecules are prepared as pure compounds or as mixtures in a combinatorial fashion.

BACKGROUND OF THE INVENTION

The strategy of targeting transcription using small molecule therapeutic agents that bind to specific RNAs can be applied to the field of antivirals. Human immunodeficiency virus (HIV) is the infectious agent responsible for acquired immunodeficiency syndrome (AIDS). Replication of the virus is dependent on specific interactions between viral ribonucleic acids (RNAs) and viral proteins. For example, one such crucial interaction is between the protein Rev and the virally encoded RNA sequence termed the Rev responsive element (RRE). The REV/RRE interaction is deemed to be critical for viral replication and has been described as the "Achilles' heel" of the virus. Dr. F. Wong-Staal has said that the REV/RRE interaction represents "the best target" for anti-HIV drug design. (Cohen, J., *Science,* 1993, 260, 1257.) The importance of the REV/RRE interaction has been established by two methods: 1) Using antisense directed at the Rev mRNA, Matsukura and coworkers (Matsukura, M., et al., *Proc. Natl. Acad. Sci. USA,* 1989, 86, 42444248) decreased the expression of the Rev protein; and 2) Expression of dominant negative mutants of the viral regulatory protein abolishes Rev activity in a cotransfection assay. (Malim, M. H., et al. *Cell,* 1989, 58, 205–214.; Bevec, D., et al. *Proc. Natl. Acad. Sci. USA,* 1992, 89, 9870–9874.) However, both methods are severely limited as therapeutic approaches as they require delivery of very large biomolecules to the infected cells of the patient.

In order to address HIV resistance it is likely that new therapeutic approaches will require combination therapy. Inhibition of the REV/RRE interaction with small orally active molecules will be very appropriate for such combinations because their mode of action and locus of activity are quite distinct from reverse transcriptase and protease inhibitors.

Experiments from the laboratories of Zapp and coworkers (Zapp, M., et al. *Cell,* 1993, 74, 969–978) have demonstrated, for the first time, that a small molecule, the aminoglycoside antibiotic neomycin B, could disrupt the REV/RRE interaction. This work of Dr. Michael Green and coworkers at the Howard Hughes Medical Institute, University of Massachusetts Medical Center has demonstrated that a limited structure activity relationship (SAR) for the inhibition of the REV/RRE interaction can be based on bioactivity data obtained from commercially available aminoglycoside antibiotics and from neomycin analogs that have been prepared. However, the structures of the aminoglycoside antibiotics are synthetically challenging and do not lend themselves to the rapid preparation necessary for a medicinal chemistry program. RNA targeted approaches are similarly suited to many other viral targets, such as Hepatitus B and C.

Ribonucleic acid plays a central role in the life of organisms from bacteria to humans. RNA serves as the intermediary between DNA and protein, the final product of gene expression and another primary building block of all living things. DNA is transcribed into a complementary RNA strand carrying the protein blueprint. The RNA interacts with ribosomes and is translated into protein. Each RNA can be translated into many copies of protein, so a small amount of RNA leads to a large amount of protein.

However, RNA is not just a transient messenger in this process. RNA directly controls gene expression by catalyzing the processing and translation of messenger RNA into protein. Ribosomes are massive ribonucleotide complexes, involving multiple protein-RNA interactions, in which RNA forms the core catalytic component. RNAse P is a smaller ribonucleotide complex that is critical for the processing of multiple RNAs such as tRNAs and 4.5S rRNA. Furthermore, RNA has been shown to play a critical role in regulation of the synthesis of ribosomal proteins from at least 5 different operons encoding ribosomal proteins and RNA polymerase subunits. Thus, RNA not only plays a critical role in the translation process but also regulates the synthesis of the translation machinery. RNA is clearly a central player in the regulation of the most fundamental processes of the cell.

Interest in targeting RNA emerged in the mid-1980's with the discovery of antisense oligonucleotides. These antisense oligonucleotides are large molecule, synthetic fragments that are designed to bind to RNA for the purpose of inhibiting or regulating its activity. While the approach of using antisense oligonucleotides is promising, to date the technology has not yielded any approved drugs. Two critical challenges in the development of antisense oligonucleotides remain: 1) effective delivery of these macromolecules into the cell, and 2) the development of new technology for the appropriate manufacture of large quantities of material.

The design of antisense molecules is based on the assumption that RNA is a linear, unfolded template without structure. The unexpected discovery by Cech and Altman (McClure, W. R., et al., *J. Biol. Chem.,* 1978, 253, 8949–8956.; Altman, S., et al., FASEB J., 1993, 7, 7–14.) of catalytic RNA, however, has forever changed this view. Their studies sparked a flurry of investigations into the structure and function of RNA that have led to unexpected demonstrations of the enormous plasticity of RNA.

Despite the existence of tRNA x-ray crystal structures, the compact, stable structure of tRNA was not considered representative of other, larger RNA species. It was not until the advent of nuclear magnetic resonance that scientists were able to determine and appreciate the complexity, rigidity and diversity of RNA structures in general. This diversity endows RNA with its extraordinary functional versatility. RNA exists in both single stranded and helical duplex forms. These duplexes are distorted by loops, bulges, base triples and junctions between helices. The structural diversity of RNA is far greater than that of DNA, and similar to that of proteins, making RNA a suitable target for small molecule drugs. Facile methods for crystallizing RNA have now been developed, which will greatly advance the understanding of RNA structure and function (Doudna et al., *Proc. Natl. Acad. Sci. USA*, 1993, 90, 7829–7833).

These recent advances in understanding the function and structure of RNA have provided a foundation for discovery and development of small molecule compounds that bind to and regulate RNA function. Small molecules have important advantages over antisense oligonucleotides and currently represent the vast majority of therapeutic compounds. Many small molecule drugs are active for oral administration and can be produced through conventional chemical synthesis techniques.

Small molecules can bind RNA and block essential functions of the bound RNA. Examples of such molecules include erythromycin, which binds to bacterial rRNA and releases peptidyl-tRNA and mRNA, and aminoglycoside antibiotics, which bind to the decoding region of 16S rRNA and cause a misreading of mRNA codons during translation. Both genetic and biochemical experiments confirm the specificity of these interactions. Also, unequivocal evidence supports the binding of thiostrepton to a specific site in 23S rRNA. Bacterial resistance to kanamycin and gentamicin maps to the specific methylation of 16S rRNA. Aminoglycosides have been chemically footprinted on 16S RNA in the absence of ribosomal proteins. Green and co-workers have shown that 2-DOS-containing aminoglycosides bind specifically to the HIV RRE, block binding of the HIV Rev protein to this RNA, and inhibit HIV replication in tissue culture cells (Zapp, Stern and Green, 1993). (Zapp, M. et al. *Cell,* 1993, 74, 969–978.) The specificity and affinity of small molecule ligands of specific RNAs have also been demonstrated by the selection of aptamers, RNAs that have been selected from populations of random sequence RNA molecules for affinity to a specific, small molecule ligand. Many of these aptamers bind with high affinity to their cognate small molecule ligand. Examples of small molecule aptamers include RNAs with high affinity for the dyes Cibacron Blue 3G-A and Reactive Blue 4, cyanocobalamin, and theophylline. The ability of RNA to distinguish between two closely related molecules is best demonstrated by the ability of the theophylline aptamer to discriminate between theophylline and caffeine, which differ by only a single methyl group.

In light of these advances, it is apparent that targeting RNA (mRNA, tRNA, rRNA, etc.) should provide effective methods for the design of new therapeutics.

Inhibition of RNA polymerase in bacteria is one of the many enzyme inhibition targets that can be addressed by screening a universal combinatoral library. A single, multi-subunit enzyme is responsible for all RNA synthesis in bacteria. RNA polymerase is a good target for antimicrobial therapy, because transcription is an essential process in the bacterial life cycle. Thus, this approach also has the advantage of allowing the selection of agents that will have a high probablity of being bactericidal rather than bacteriostatic, in contrast to current cell-based assays, which do not distinguish between bacteriostatic and bactericidal compounds. Because the bacterial polymerase differs significantly from the mammalian polymerase, it is possible to develop inhibitors with low toxicity. In addition, because the RNA polymerases of different bacterial genuses have high sequence homology the development of broad-spectrum antibiotics is feasible. Another advantage of this approach is that it targets a metabolic pathway different from those most often affected in cell-based assays, primarily the cell wall and membrane biosynthesis, leading to novel agents with decreased liability for bacterial resistance. Fungal RNA polymerase, similarly, provides a target for antifungal drug discovery.

Traditionally, drug discovery efforts have involved the random screening of natural product extracts or synthetic compound libraries for a desired bioactivity, with medicinal chemistry then being used to optimize the pharmacological and toxicological profiles of the lead compound. With the recent advances in automation and screening technology, the rate at which this process can occur has become limited by compound library availability. In response to this need, a field of chemistry termed combinatorial chemistry has arisen with its objective being molecular diversity generation. The libraries that have been created to date have followed two distinct logical patterns. The first is to mimic the diversity generated in nature by using a limited number of monomeric units (i.e.,. 4 nucleotides, 20 amino acids) and allowing oligomerization to generate the diversity. Originally, the libraries created were either peptides or nucleic acids. However, these types of compounds are usually not acceptable drug candidates due to their poor bioavailability and metabolic susceptibility. The technological advancements afforded by these early combinatorial methods opened the door for the next generation of libraries. The chemistry was developed based on peptide mimetic monomers which when oligomerized became compounds that were not expected to suffer the same biological profiles as their predecessors. Examples of the types of monomeric units that constitute the backbones of these libraries include carbamates, N-substituted glycines, aminimides, and vinylogous amides. While these libraries are certainly useful for in vitro screening, they may, and often do, still possess less than the optimal bioavailability and pharmacokinetic parameters required for oral delivery of drugs. Also, being roughly linear oligomers with limited ability to access the secondary and tertiary structures required for the selective binding observed in natural systems, and not having the thermodynamic advantage of a rigid 3-D structure which is preorganized for the desired binding mode, these library motifs all sample similar molecular space. Consequently, lead compounds isolated from these libraries still require substantial optimization in an ensuing medicinal chemistry program.

Many orally available drugs possess a molecular weight of less than about 500 daltons and routinely contain heterocyclic rings to improve their bioavailability, ease of synthesis, and toxicological properties. These are two of the requirements that are the driving force behind the second major ideological thrust in combinatorial science. Small molecule libraries based on a central molecular scaffold which is subsequently functionalized with pendant groups are currently the subject of a great deal of investigation. There are examples of small molecule libraries that have been prepared by either solid or solution phase chemistry to generate compounds either singly or as mixtures. Examples of the types of molecules that vary around a central core that have been prepared in a combinatorial fashion include benzodiazepines, hydantoins, tetrahydrofurans, xanthines, and cubanes. A distinct advantage to this approach is that a lead structure identified by the screening of these libraries may require less extensive modification in a medicinal chemistry program to produce a drug candidate. Of critical importance in the generation of materials in a combinatorial manner are the questions of coordinate space being searched and diversity of analog functionality. Diversity of physical dimension (X, Y, Z) is important but should be considered in conjunction with molecular properties such as charge, hydrogen bond forming capability, and hydrophobicity/ hydrophilicity. The small molecule libraries that currently exist are based either on aromatic scaffolds which impart a planar shape to the analogs prepared, di-functionalized tetrahydrofurans whose derivatives mimic the shape of nucleotides, or poly-functional derivatives of cubane.

The aminocyclitol, 2-deoxystreptamine, spatially resembles a saccharide unit. Molecules that resemble saccharides while lacking the C-1 hemi-acetal found in natural saccharide units, are known competitive inhibitors of a large number of enzymatic systems, especially the glycosidase and glycosyl transferase enzymes. Molecules of this type bind to the active site of the enzyme but are inert to enzymatic transformation. Oligosaccharide portions of glycoproteins and glycolipids located at the cell surface have been associated with such diverse membrane functions as intercellular communication and adhesion of cells, the immune response, and malignancy. The introduction of synthetic sugar analogs into the cell that can regulate the enzymes responsible for biosynthesis of these membrane components has been shown to be an effective method for altering membrane structure and function. However, the number of available non-natural oligosaccharide analogs that can be screened for their inhibitory effects in the cell remains relatively small. This is in part due to the tremendous difficulty associated with oligosaccharide synthesis. The rapid generation of oligosaccharides, and oligosaccharide analogs, is a topic of much current interest. Efforts toward the automated (solid phase) syntheses of oligosaccharides are underway, but this approach has some limitations (such as the inability to prepare anomeric linkages of the β-configuration) and is currently of little utility. In an effort to circumvent the hurdles of oligosaccharide synthesis, a combinatorial approach to oligosaccharide analogs can be conveniently based on 2-deoxystreptamine as disclosed herein.

In addition to the combinatorial generation of possible drug candidates, functionalized derivatives of 2-deoxystreptamine are useful in the field of separation science. Often a very useful source of information for the performance of rational drug discovery is the structure of the biological ligand acceptor. Information obtained by testing combinatorial libraries can be used in conjunction with molecular modelling calculations to simulate modes of binding of the guest ligand to the biological host. The information can then be used to generate hypotheses for structural change of the ligand that are anticipated to enhance affinity.

Unfortunately, the determination of the structures of biological acceptors/receptors or receptor-ligand complexes is an arduous task that requires the purification of the acceptor from the biological milieu from whence it came. Routinely, this purification will entail several types of chromatographic separation as the grail of on-demand biological macromolecule crystallization has yet to be attained.

Chromatographic separations are the result of reversible, differential binding of the components of a mixture to an active surface as the mixture in solution elutes over that surface. Compounds experiencing the greatest associative interaction with the active surface of the solid support will be retained and thereby separated. In the majority of cases, prior art support materials were developed with a specific purpose, or purposes, in mind and are of limited utility. Standard supports used in chromatography, such as reversed phase silica, can denature proteins and often require the use of organic solvents or buffered pH conditions that are incompatible with sensitive biomolecules. When a chromatographic support is derivatized with molecules which bind specifically to a component of a complex mixture, that component will be separated from the rest of the mixture and can be eluted subsequently by an appropriate change in the eluent (ionic strength, pH) that will disrupt the interaction between support and substrate. This so called affinity chromatography is a widely used method for the purification of biological molecules. The development of substances/supports to be used in separations of this type would be very useful.

"Molecular recognition" is a term used to describe the myriad forces that govern the interactions between molecules. Most commonly, this term is applied to the attractive association between two biological macromolecules (e.g., protein-protein, protein-nucleic acid, or nucleic acid-nucleic acid), or to the binding of a small molecule ligand (guest) to a larger macromolecular binding site (host). Often, small molecules can mimic proteins or nucleic acids in their interactions with a binding site and interfere competitively with the macromolecular associations mentioned above. These types of recognition events are at the heart of the drug discovery process. Screening of natural product extracts and random synthetic libraries, for small molecule guests that demonstrate affinity in vitro for a pharmacologically significant macromolecular host has historically been the source of lead molecules in the pharmaceutical industry. Compounds that demonstrate the desired biological activity are then structurally modified, together with what is known about the structure of the binding site, in an effort to optimize their affinity and specificity for the host. This process continues iteratively to generate a structure/activity relationship (SAR) that leads eventually to an optimal drug candidate. This series of events can be performed much more rapidly, and less empirically, if structural data exists for the host or for the natural ligand. Unfortunately, detailed structural information about the biological host is routinely unavailable. Recently, with the advent of automated screening technology, the rate limiting step in the drug discovery process has become the preparation of analogs of an active lead to investigate the structure/activity relationship. The response of the medicinal chemical community to this need has been the active development of a field of chemistry termed combinatorial chemistry.

The various properties of a molecule that can be modified during the course of analog preparation include ionic interactions, hydrogen bonding capability, hydrophobicity, n stacking interactions, Van der Waals or steric interactions with the host, and reorganization of the molecule into a conformation resembling the bound conformation a natural ligand.

SUMMARY OF THE INVENTION

The subject invention provides compounds which are useful as pharmaceuticals and as pharmaceutical lead compounds, including but not limited to RNA-targeted agents, antivirals, antibacterials, and/or antifungal agents. These compounds have the formula:

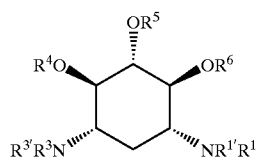

wherein $R^1$ and $R^3$ independently are hydrogen, —CHO, —COCH$_3$, —COR$^7$, —COCCl$_3$, —COCF$_3$, benzyloxycarbonyl (CBZ), t-butoxycarbonyl (t-BOC), fluorenylmethyloxycarbonyl (F-moc), a d or l amino acid, a peptide, -D-(Q)$_x$ or -A-Ar-(Q)$_z$.

D is a linear, branched or cyclic group having from 4 to about 15 atoms selected from the group consisting of C, N, O, S, P and any combination of the foregoing; wherein D is unsubstituted or substituted with one or more groups independently selected from the group consisting of =O, —OH, =NH, NH$_2$, —NHR$_7$, —NHR$_7$R$_8$, alkyl and =CH$_2$. The number of groups can be varied based on the oxidation states available to each atom and may optionally be substituted.

Each Q is independently selected from the group consisting of —CNH(NHY), —NHCNH(NHY), —NHCO(NHY), —CONHY, —COOH, —COOY, —NHCOY, —NHSO$_2$Y, halogen, —CN, —NO$_2$, —SO$_2$W, —SOW —OPO$_3$, imidazolyl, thiazolyl, pyridyl and indolyl.

Y is selected from the group consisting of hydrogen, alkyl, alkenyl, —B—NH$_2$, —B—NHR$^8$, —B—NR$^8$R$^9$, —B-aryl, —B-substituted aryl, —B-morpholino or —B-pyridyl.

A and B independently are a bond, or a linear, branched, or cyclic linking group having from 1 to about 15 atoms selected from the group consisting of C, N, O, S, P and any combination of the foregoing; wherein A and B independently are unsubstituted or substituted with one or more groups independently selected from the group consisting of =O, —OH, =NH, NH$_2$, —NHR$_7$, —NHR$_7$R$_8$, alkyl, and =CH$_2$. The number of groups can be varied based on the oxidation states available to each atom. Ar is an aryl or heteroaryl group. W is selected from the group consisting of alkyl, alkenyl, —B—NH$_2$, —B—NHR$^8$, —B—NR$^8$R$^9$, —B-aryl, —B-substituted aryl, —B-morpholino or —B-pyridyl.

$R^7$ represents an alkyl, a branched alkyl, a cycloalkyl or an aryl group.

$R^8$, $R^9$ and $R^{10}$ are independently represented by hydrogen, alkyl, branched alkyl, or cycloalkyl, or aryl groups; x is 0, 1 or 2; and z is 0, 1, 2, 3 or 4.

$R^{1'}$ and $R^{3'}$ are independently selected from the group consisting of hydrogen, alkyl, and benzyl or alternatively $R^1$ and $R^{1'}$ or $R^3$ and $R^{3'}$ with their respective nitrogen atoms independently form a phthalimido, succinimido, 2,5-dimethylpyrrolo- or N-1,1,4,4-tetramethyldisilylazacyclopentane group.

$R^4$, $R^5$ and $R^6$ independently are selected from the group consisting of hydrogen, —CHO, —COCH$_3$, —COR$^7$, —COCCl$_3$, —COCF$_3$, a d or l amino acid, a peptide, a natural or non-natural saccharide, aminosaccharide, oligosaccharide, oligo-aminosaccharide, -D-(Q)$_x$ and -A-Ar-(Q)$_z$, where A, D, Ar, Q, Y, R$^7$, x and z are as defined above. The saccharide groups are typically linked at the one position of the saccharide unit.

$R^4$ and $R^5$, or $R^6$ and $R^5$, taken together comprise a methylidene, ethylidene, isopropylidene, cyclohexylidene or benzylidene bridge, and the $R^3$ and R4 groups, or $R^1$ and $R^6$ groups, independently, taken together may comprise an intramolecular carbamate;

with the proviso that at least two of $R^1$, $R^{1'}$, $R^3$, $R^{3'}$, $R^4$, $R^5$ and $R^6$ are not hydrogen.

Further contemplated by the present invention are pharmaceutical compositions which comprise these compounds.

The compounds of the invention are also useful in chromatographic supports. These compounds can be linked to a solid chromatographic support through one of the attached groups. For example, $R^1$ or $R^3$ can be a urea, carbamate, or 2-hydroxyalkylamino linkage to a support and $R^{1'}$ and $R^3$ can each be hydrogen. This will provide a chromatographic support having the formula:

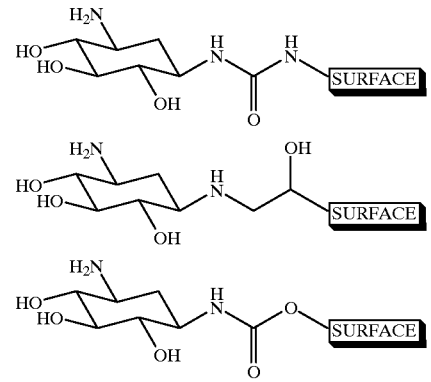

Additionally, the linkage can be through a group attached to one of the oxygen atoms. For example $R^4$, $R^5$, or $R^6$ can be a carbonate linkage to a polymeric support. An example of a support having an oxygen linkage is shown below.

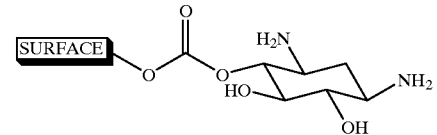

The preparation of structurally and functionally diverse molecules based on the molecular scaffold of 2-deoxystreptamine is disclosed. These molecules can be prepared in a combinatorial sense to afford mixtures (of constituency around 10) which can then be assessed in biological/pharmaceutical screens as part of a drug discovery program. These compounds can also be prepared singly in pure form for screening, for further testing, or to be used as medicaments. Said pure compounds, or mixtures thereof, may also be appended to a solid support, either directly or through a tether, or incorporated into polymers or gels to afford novel substances that could have utility in the fields of separation science and in the development of diagnostic materials. Said substances or gels could exhibit utility as affinity chromatographic supports.

DETAILED DESCRIPTION OF THE INVENTION

Figure 1A:
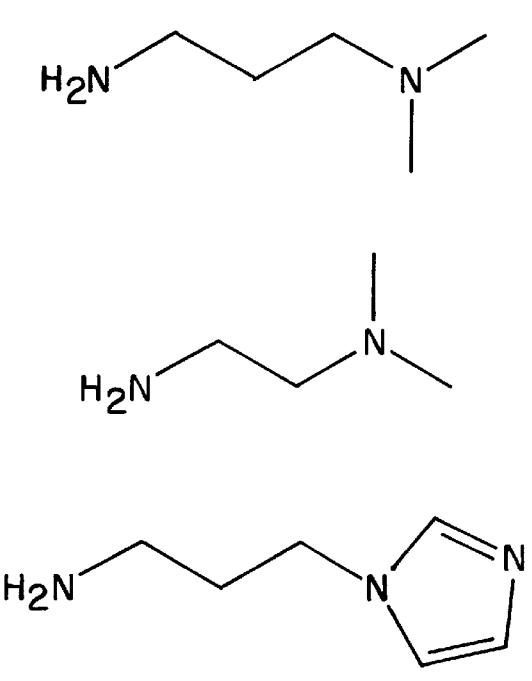
FIGS. 1A–6B illustrate amines used in the diversity-generating reaction mixtures.

The subject invention is based in on the discovery that:
1) 2-Deoxystreptamine is a stable, polyfunctional amino cyclitol that is present in many naturally occurring and clinically useful amino glycoside antibiotics.
2) 2-Deoxystreptamine is chemically and conformationally stable, polyfunctional, and amenable to a wide variety of regio- and chemoselective chemical transformations.
3) Compounds based on 2-deoxystreptamine, when shown to have a specific affinity for another molecule/substance, can be readily appended to solid supports, either directly or through a tether, to afford novel materials capable of molecular recognition, useful as, including but not limited to, solid supports for chromatography, catalysts, solid phase immunoassays, and materials designed for the for use in the separations of various components of complex mixtures Combinatorial libraries based on the amino cyclitol 2-deoxystreptamine add to the regions of conformational space that can be searched for biological activity. The presence of the scaffold unit taken from the amino glycosides, which interact with RNA, is expected to make these compounds useful in the discovery of novel RNA-interactive agents. The wealth of chemistry that can be used to functionalize the 2-deoxystreptamine scaffold coupled with the ability to control regiospecifically the additions allows for the generation of materials that are structurally diverse, and therefore sample substantially different conformational space than other known libraries. The use of 2-deoxystreptamine as the scaffold for the generation of small molecules will provide libraries that will effectively probe all space within a 25 Å spherical or torus shaped area. The use of 2-deoxystreptamine as a scaffold for the generation of molecular diversity allows us to investigate these molecular properties in a combinatorial fashion. Random libraries of small molecules based on 2-deoxystreptamine are able to incorporate any, or all, of these possible interactions into the development of a structure activity relationship.

Derivatization of solid supports with a specific ligand based on 2-deoxystreptamine, which has previously been shown to have a preferential affinity for a particular constituent of a biological mixture, would afford an affinity chromatography column for that host that can be used under extremely mild non-denaturing conditions. The synergistic effect produced by the rapid combinatorial generation of molecules based on 2-deoxystreptamine coupled to the use of active library members as separatory tools for screening reagent preparation is extremely powerful.

Another application where small molecule-derivatized surfaces have become useful is in the determination of the nucleotide sequences that form the preferential binding site of a DNA, or RNA, host for a natural or non-natural ligand. This technique is called a SELEX experiment and involves the derivatization of a solid support with a known ligand that exhibits preferential affinity for a nucleic acid binding site of unknown sequence. A complex mixture of oligonucleotide fragments is then passed through the column with the fragments that experience some association to the ligand being preferentially retained. Subsequent elution of the retained fragments followed by PCR amplification (polymerase chain reaction amplification) provides a sample that has been considerably enriched in the binding site sequence of the host. Several rounds of affinity chromatography, elution, and amplification afford a sample that can be sequenced using standard molecular biology techniques. Once again, derivatization of solid supports with a specific ligand based on 2-deoxystreptamine, which has previously been shown to have a preferential affinity for a biologically important oligonucleotide of unknown sequence, would afford an affinity chromatography column for that nucleotide that can be used for SELEX sequence determination.

Examples of groups suitable for incorporation in either or both A and B include but are not limited to such groups as, for example,

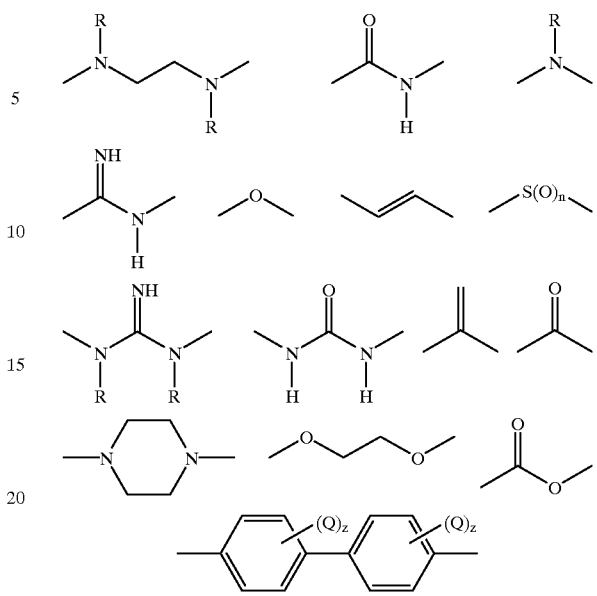

and the like, wherein R represents a lower alkyl group and n is 0, 1 or 2.

Examples of the Q groups include but are not limited to groups, such as, for example, —CNH(NHY), —NHCNH (NHY), —NHCO(NHY), —COOH, —NHCOY, —NHSO$_2$Y, —SO$_2$W, —SOW and the like. Preferred Q groups are —CNH(NHY), and —NHCNH(NHY). The preferred Y groups are hydrogen, alkyl and aminoalkyl.

The aryl and heteroaryl groups can have from 6 to about 10 carbon atoms and one or two rings. Preferably the aryl groups will have from 1 to about 6 carbon atoms. These groups include substitution at all positions such as, for example, 2-, 3-, and 4-pyridyl. Examples of suitable aryl and heteroaryl groups include but are not limited to groups, such as, for example,

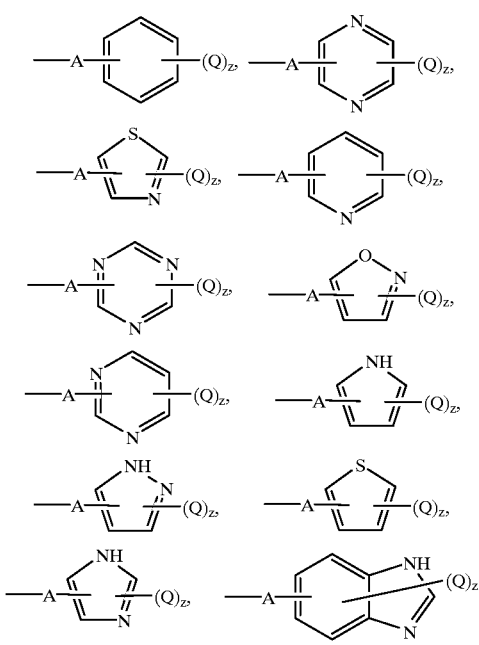

-continued

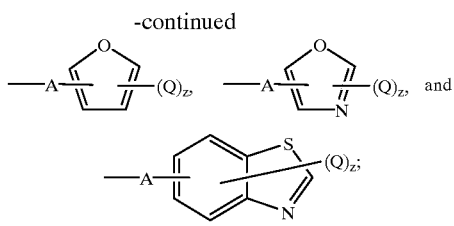

and the like. Preferred aryl and heteroaryl groups have formulas:

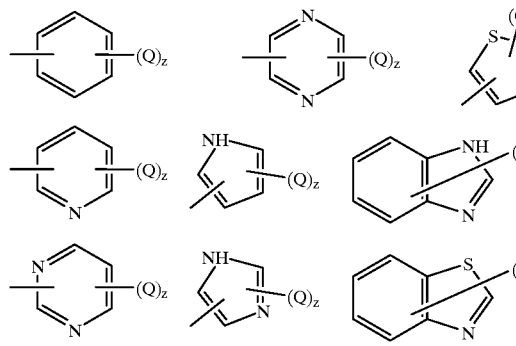

The most preferred aryl or heteroaryl groups have formulas:

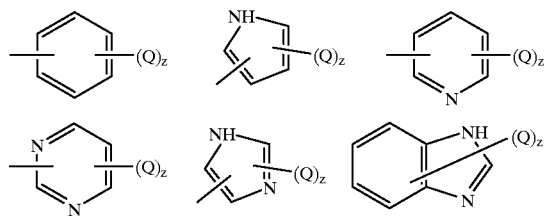

The alkyl and alkenyl groups can be straight chain, branched, or cyclic groups. These groups can have from 1 to about 18 carbon atoms. Preferably the alkyl and alkenyl groups will have from 1 to about 8 carbon atoms. Most preferably the alkyl groups will have from 1 to about 6 carbon atoms.

The cycloalkyl and cycloalkenyl groups can have from 3 to about 15 carbon atoms and one or two rings. Preferably the cycloalkyl and cycloalkenyl rings will have from 3 to about 8 carbon atoms.

Preparation of 2-Deoxystreptamine

The aminocyclitol 2-deoxystreptamine 1 is obtained by the acid degradation of neomycin B by heating the neomycin in a concentrated hydrobromic acid solution (see Scheme 1). The reaction is followed by ion exchange chromatography to afford the free base of 1. The procedure is amenable to the preparation of hundred gram quantities. Most other aminoglycoside antibiotics contain the 2-deoxystreptamine moiety and are also suitable substrates for the degradation reaction.

Scheme I

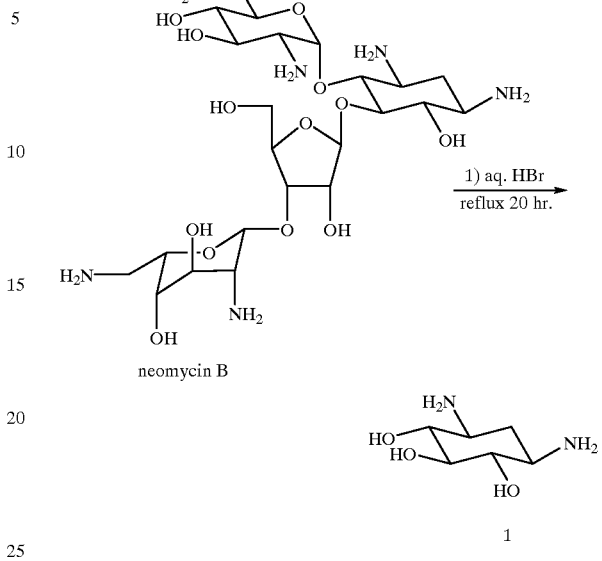

N-Functionalization of 2-Deoxystreptamine

The abundant functionality found on the 2-deoxystreptamine molecule allows for derivatives of widely varying complexity to be prepared. Selective functionalization of the 1- and 3-position nitrogen atoms in the presence of the unprotected 4, 5, and 6 position oxygens is readily effected. Exposure of 2-deoxystreptamine to alkyl halides results in the formation of bis-quaternaryammonium salts with potential uses in the areas of surface science and catalysis. This reaction is as follows:

Scheme II

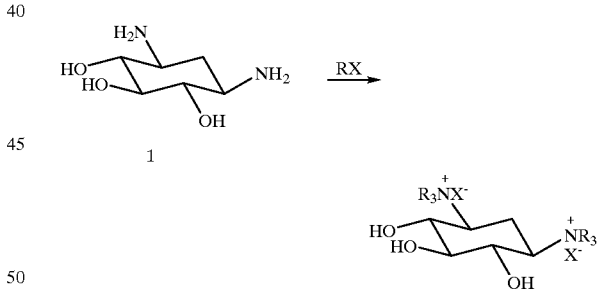

wherein $R^3$ is as defined above. The nitrogen atoms are amenable to acylation with two equivalents of an acylating agent such as, for example an acyl halide or anhydride, affording bis-amido structures. Molecular diversity can be generated by the treatment of 2-deoxystreptamine with mixtures of acylating agents (range 1–5, preferably 3, reagents per reaction) to generate mixtures of bis-amido compounds that contain, in the case of three reagents, 6 compounds, 3 of which are meso, and 3 of which are racemic, for a total of 9 separate chemical entities per reaction. Acylating agents should be grouped in mixtures according to their reactivity and stoichiometry must be rigorously controlled so that all constituents of the product mixture will be represented equivalently. The reaction is as follows:

Scheme III

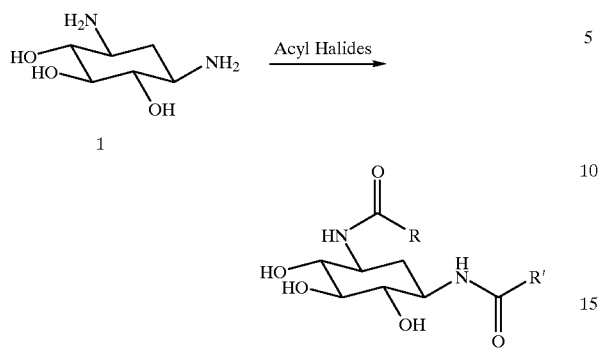

wherein R and R' are appropriate hydrocarbyl groups. 2-Deoxystreptamine is also readily acylated with natural and/or non-natural aminoacids or peptides through the use of the activated ester technologies or from the corresponding amino acid acylhalides. Molecular diversity can be generated by the treatment of 2-deoxystreptamine with mixtures of acylating agents, preferably 3, reagents per reaction to generate mixtures (in the case of 3 reagents) of approximately 10 separate chemical entities per reaction. The reaction is as follows:

Scheme IV

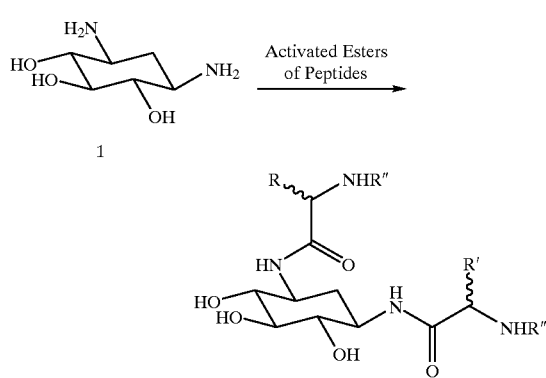

wherein R" and R'" are the groups which form the remainder of the amino acid or peptide. The amine groups of 2-deoxystreptamine may also be functionalized as carbamates affording bis-carbamoyl structures. Molecular diversity can be generated by the treatment of 2-deoxystreptamine with mixtures of from 1 to 5 carbamoylating agents preferably 3, reagents per reaction to generate mixtures of bis-carbamoyl compounds that in the case of 3 reagents contain 6 compounds, 3 of which are meso, and 3 of which are racemic, for a total of 9 separate chemical entities per reaction. Carbamoylating agents should be grouped in mixtures according to their reactivity and stoichiometry must be rigorously controlled so that all constituents of the product mixture will be represented equivalently. The reaction is as follows:

Scheme V

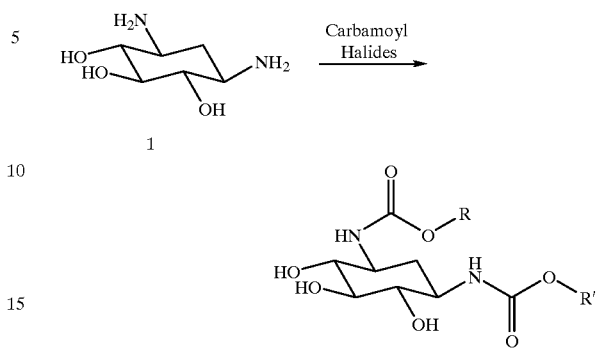

wherein R and R' are appropriate hydrocarbyl groups.

Further diversity can be generated as the chemistries described above for the functionalization of the amine groups of 2-deoxystreptamine are also compatible with one another such that mixed derivatives can be prepared (i.e.,. acyl-peptide, or peptide-carbamate derivatives).

Treatment of bis-carbamoyl-2-deoxystreptamine derivatives with strong base affords the bis-intramolecular carbamate derivative shown below. This derivative is a useful intermediate leading to regiochemically controlled oxygen substitutions, as well as affording a convenient means for the attachment of 2-deoxystreptamine derivatives to solid supports.

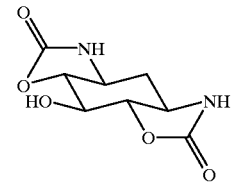

In many of the preparations of combinatorially diverse 2-deoxystreptamine derivatives, the nitrogen atoms can be protected prior to functionalization of the oxygens. The methods described above encompass the more common methods of nitrogen protection but in each case the nitrogen still possesses one hydrogen. Several of the oxygen functionalization procedures being disclosed herein may require that both of the hydrogens of the amine groups be removed by the protective scheme. Derivatives which satisfy this criterion are bis-phthaloyl, -succinoyl, 2,5-dimethylpyrrolo, and -N-1,1,4,4-tetramethyl-disilylazacyclopentane derivatives. Examples of these compounds are shown below:

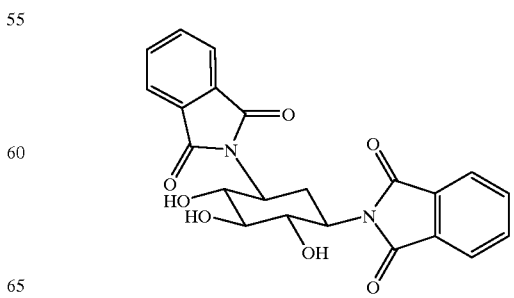

Bis-phthaloyl-2-deoxystreptamine

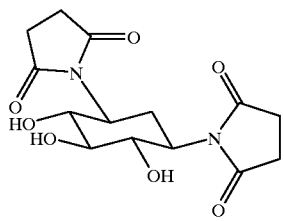

Bis-succinoyl-2-deoxystreptamine

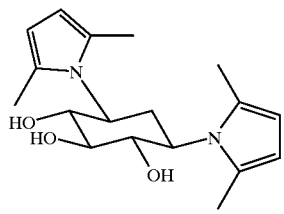

Bis-2,5-dimethylpyrolo-2-deoxystreptamine

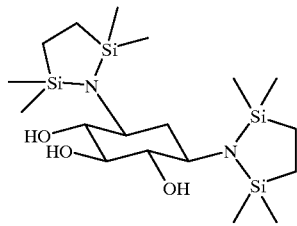

N,N'-1,1,4,4-tetramethyldisilylazacyclopentane-2-deoxystreptamine

O-Functionalization of 2-Deoxystreptamine

Functionalization of the hydroxyl groups of 2-deoxystreptamine can occur under a variety of conditions; however, any chemistry requiring an oxygen atom of the hydroxyl groups to function as a nucleophile will involve the use of a protective group to mask the amine groups. Any standard methods used to protect amines including methods that remove either one or both of the protons of the amine are suitable. Compounds can be prepared by the treatment of a bis-amino protected 2-deoxystreptamine derivative with mixtures of from one to three reagents for O-functionalization, preferably three, to generate mixtures of products containing, in the case of three reagents, 27 distinct chemical entities per mixture, 9 of which are meso, and 18 of which belong to 9 enantiomeric pairs. The reagents for simultaneous per-O-functionalization of the 2-deoxystreptamine triol are chosen such that the reaction conditions for the pendant group introductions are similar. For example, acylating reagents such as acyl halides, anhydrides, and carbamoyl chlorides can be introduced simultaneously under standard conditions, as can alkyl, aryl, benzylic, and acetophenone groups by way of their halides.

Inclusion of pendant groups from multiple classes of reagents using different chemistries and/or control of the regiochemistry of substitution require that functionalization of the hydroxyl groups occur in a stepwise manner. This allows for the generation of much greater diversity than would be available using only one class of reagents. Secondly, the ability to prepare analogs in the mono- and di-substituted (both 4,5 and 4,6) 2-deoxystreptamine manifolds becomes available. Finally, and lastly, after the library of mixtures has been screened for activity in a biological assay and the identity of the constituents of any mixtures exhibiting activity has been determined, the individual constituents of the mixture will have to be prepared singly for further testing. The ability to prepare in pure form any molecule in the library is an essential element in the deconvolution of the mixtures. The protective strategies for the regiochemical control of hydroxyl group functionalization are described below. Differentiation between the 5 position hydroxyl and the 4- and 6-position hydroxyl groups can be achieved by the preparation of a bis-intramolecular carbamate 2-deoxystreptamine derivative as shown below. This is conveniently done by treatment of a 2-deoxystreptamine di-carbamate with a strongly basic ion exchange resin to effect the intramolecular ring closure. The intramolecular carbamate can then be functionalized at the 5 position selectively. If the 5 position is to remain as a hydroxyl group in the library being generated, then the 5 position can be selectively protected at this point. Formation of the trimethylsilylethyl ether protective group for this position proceeds in high yield and can be removed chemoselectively from other protective groups. Subsequent carbamate ring opening of the derivative that has either been functionalized or protected at the 5 position is readily performed by treatment with an alkoxide to regenerate a carbamate protective group on the amine functionality and to simultaneously liberate the vicinal (4 and 6 position) hydroxyl groups for further elaboration.

Scheme VI

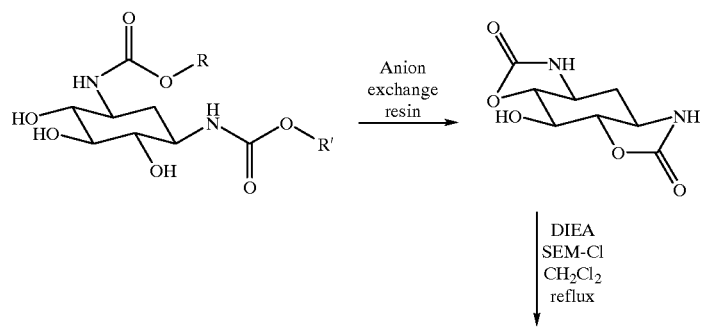

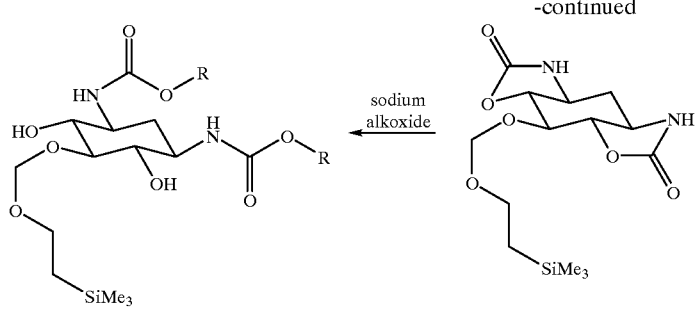

If further differentiation of the hydroxyl groups is required, treatment of the 5-position protected bis-intramolecular carbamate with one equivalent of alkoxide will afford a racemic mixture of the two possible mono-intramolecular carbamates where an unmasked hydroxyl is free to be functionalized as illustrated in scheme VII.

Scheme VII

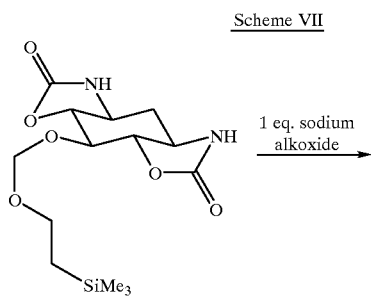

-continued

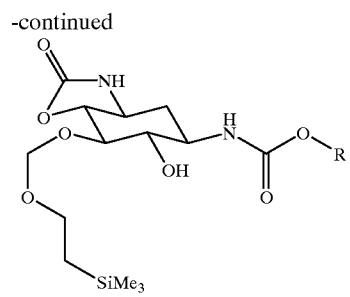

Differentiation between the 4 position hydroxyl and the 5- and 6-position hydroxyl groups, and the 6-position from the 4 and 5 positions, can be achieved by the introduction of ketal or acetal diol protective groups such as acetonide, or benzylidene onto the enantiomeric sets of vicinal diols. Bis-2,5-dimethylpyrrolo-2-deoxystreptamine, or any other N-protected derivative, may be protected as the acetonide ketal under mild conditions by treatment with 2,2-dimethoxypropane under anhydrous conditions with a catalytic amount of protic acid to afford materials such as 3 that have one remaining hydroxyl group available for derivatization (either the 4 or 6 position). Subsequent deprotection of the acetonide functionality under standard conditions affords the 4,5 or 5,6 diol for library generation. An example of this reaction is shown below:

Scheme VIII

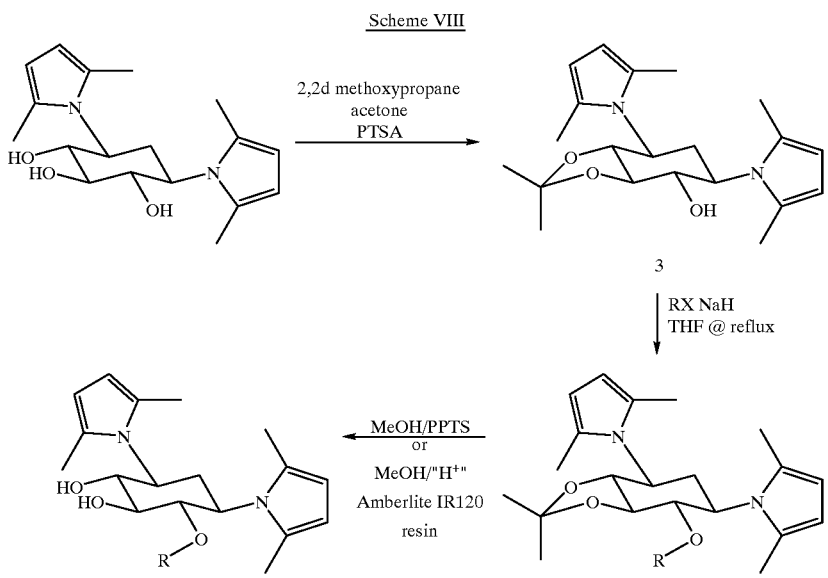

If further regiochemical control is required the 4,5 or 5,6 benzylidene acetal can be opened regiospecifically under reductive conditions to free the more sterically hindered alcohol (either the 4 or the 6) thus allowing further functionalization to occur. This reaction is shown below.

Scheme IX

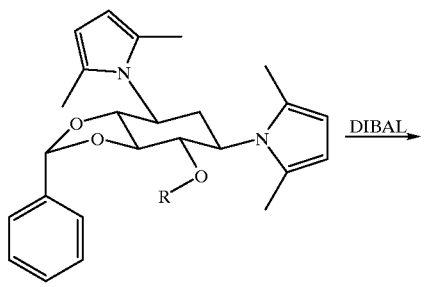

These strategies taken together allow for the preparation of single analogs of known structure.

A tremendous variety of groups which can be appended to the hydroxyl groups of the 2-deoxystreptamine core are available. The most expedient method for diversity generation is esterification; however, these analogs in their final form need to be functionalized on the two nitrogen atoms of 2-deoxystreptamine to prevent the migration of the 4 or 6 position acyl function to the amine group to form the thermodynamically more stable amide. The formula shown below generally illustrates some of the analogs which can be prepared. The compounds having n=0 are prepared by nucleophilic aromatic substitution of an appropriately substituted aromatic halide. Compounds where n=1 can be prepared by the Williamson ether synthesis. These compounds include "benzylic" materials and can have heteroatom substitution in the ring system such as picolyl, furanyl, or thiophenyl derivatives.

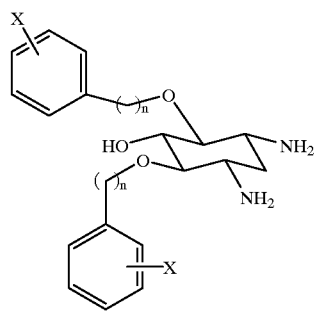

Compounds having n=2 can be prepared through transition metal catalyzed addition to olefins, reaction with haloacetophenone derivatives, or by addition to an epoxide.

Also disclosed is the preparation of aminoglycoside mimics based on 2-deoxystreptamine where the pendant functionality is a saccharide unit. There are a wide variety of glycosylation strategies available for the preparation of oligosaccharides with the choice of method being determined by the availability of the glycosyl donor (pendant group), the efficiency of the coupling in a related system in the case of nonnatural saccharides, and whether the method in question will generate a glycosidic linkage of the desired stereochemistry.

Scheme X

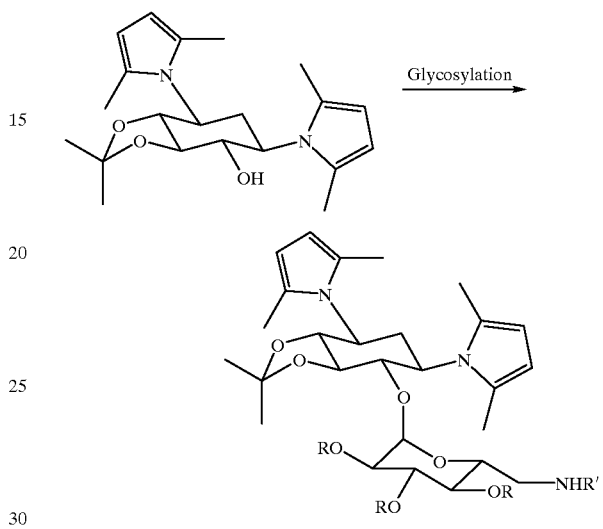

Methods for forming the glycoside include the Koenigs Knorr type coupling of an alcohol with a glycosyl halide in the presence of either a silver or mercury salt and the various improved versions of this reaction published in the scientific literature; the addition of an alcohol to a glycal or glycal epoxide; and the addition of an alcohol to the cyclic oxo-carbonium ion intermediate derived from either the Lewis acid treatment of a glycosyl-trichloroacetimidate, the bis-collidinyl iodine perchlorate treatment of a pentenyl glycoside, or the oxidation of a phenylthioglycoside to the anomeric phenylsulfoxide.

Fabrication of 2-DOS containing macromolecular structures capable of specific molecular recognition Chromatographic separations are the result of reversible, differential binding of the components of a mixture to an active surface as the mixture in solution elutes over that surface. Compounds experiencing the greatest associative interaction with the active surface of the solid support will be retained and thereby separated. When a chromatographic support is derivatized with molecules which bind specifically to a component of a complex mixture, that component will be separated from the rest of the mixture and can be eluted subsequently by an appropriate change in the eluent (ionic strength, pH) that will disrupt the interaction between support and substrate. This is referred to as affinity chromatography and is a widely used method for the purification of biological molecules. Derivatization of solid supports with a specific ligand based on 2-deoxystreptamine, which has previously been shown to have a preferential affinity for a particular constituent of a biological mixture, would afford an affinity chromatography column for that host that can be used under extremely mild non-denaturing conditions. Many solid supports that have been "pre-activated" for easy functionalization are commercially available. There are several different chemistries available for the functionalization of solid surfaces and most are offered such that linkages of variable length between the solid surface and the ligand can be prepared. 2-Deoxystreptamine-based affinity chromatography materials can be prepared in a number of ways. First, an amine of a 2-deoxystreptamine containing compound can react with a cyanogen bromide activated (cyanate) surface to afford, a carbamate linkage. This method of immobilization has been used extensively in the field of affinity chromatography and will afford a material that is stable and contains a high titer of ligand per unit volume of the resin. The preparation is shown below:

Scheme XI

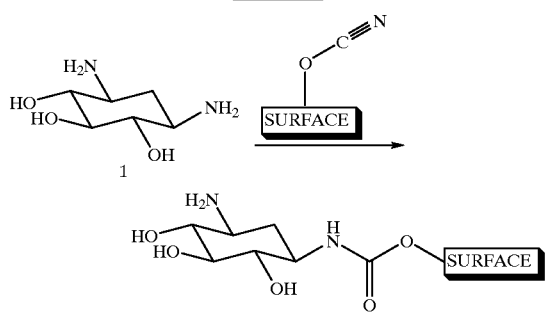

Another method for appending 2-deoxystreptamine to a solid support using one of the amine groups of the ligand involves the use of an amino surface that has been activated with p-nitrophenylchloroformate. The p-nitrophenylcarbamoyl surface is then susceptible to nucleophilic displacement of the p-nitrophenolate anion by the amine group of the ligand to provide a urea-linked 2-deoxystreptamine-functionalized surface as shown in Scheme XII below:

Scheme XII

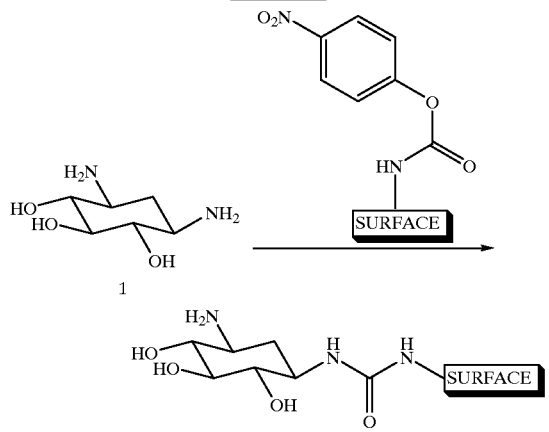

If formation of a functionalized surface that does not contain a carbonyl linkage is required, the amine group of the 2-deoxystreptamine ligand can be reacted with an oxiranyl-surface to afford a β-hydroxylamino linkage. This type of linkage creates a local environment around the ligand that is less hydrophobic than a direct alkyl linkage. This is an important consideration in protein purification applications because hydrophobic surfaces tend to have a denaturing effect on the proteins being chromatographed. The preparation of this type of linkage is shown in Scheme XIII below:

Scheme XIII

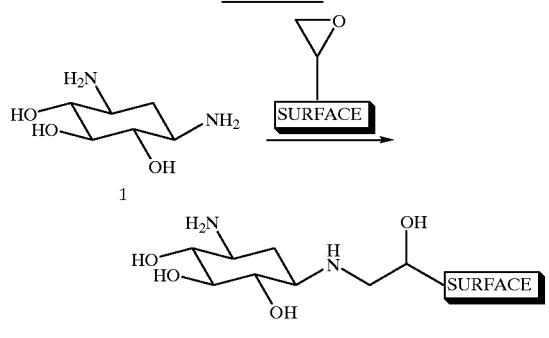

Alternatively, if the use of a protective group during the preparation of the 2-deoxystreptamine derivative precludes the use of one of the ligand amines as a nucleophile for the linkage to the solid support, commercially available amine functionalized surfaces that will react with the intramolecular carbamate formed between the vicinal amine and hydroxyl groups of 2-deoxystreptamine can be employed to afford a urea-linked functionalized surface.

Scheme XIV

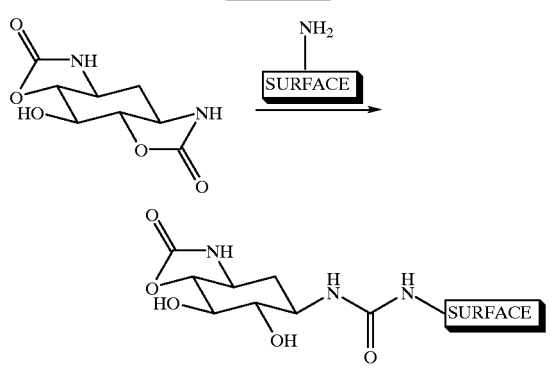

Lastly, should the derivative of 2-deoxystreptamine that requires covalent linkage to a solid support have both of its amine groups incorporated into pendant functionality that are necessary for binding the host, the derivative can be appended to an activated surface through a carbonate linkage derived from one of the hydroxyl groups of 2-deoxystreptamine and a cyanogen bromide activated (cyanate) surface as illustrated in Scheme XV, below:

Scheme XV

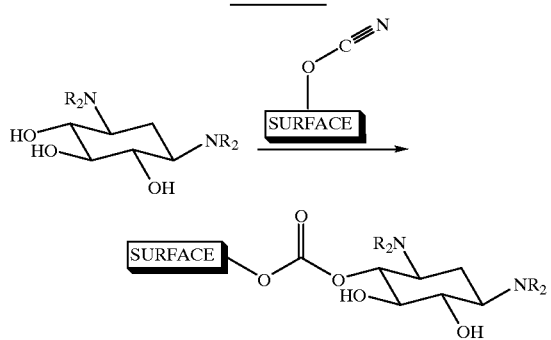

Preparation of Combinatorial Libraries of N-Functionalized 2-Deoxystreptamine.

The following procedure describes the preparation of a combinatorial library containing molecules based on the 2-deoxystreptamine scaffold that are functionalized on the amine groups of the parent scaffold. This procedure will prepare 90 different chemical entities as 10 mixtures containing 9 compounds per mixture. Into each of an array of 10 vials is placed 2-deoxystreptamine in a solvent, suitable for the chemistry to be performed. The amount of 2-deoxystreptamine used per vial is defined by the final amount required of each chemical entity to be prepared in that vial (if 2 µmoles of each compound is required for biological assay then 2-deoxystreptamine must be used at 9 times that amount per vial). The solvent to be used should preferably be both organic and water soluble, such as, for example, tetrahydrofuran (THF), dimethyl formrmide (DMF), or dimethylsulfoxide (DMSO). The nature of the appended groups will dictate the method of compound isolation (i.e.,. libraries that are expected to be water soluble are precipitated by the addition of a non-polar organic solvent (such as diethyl ether or hexanes) to the reaction mixtures. Analogously, compounds that are anticipated to be organic soluble are precipitated from the reaction mixtures by the addition of water. or brine). To the array of 10 vials that contain the 2-deoxystreptamine, at an appropriate temperature (preferably 0° C.), are added sequentially 10 different mixtures of the reagents to be appended to the 2-deoxystreptamine. These mixtures will preferably contain three different reagents. The reagents are acylating reagents, carbamoylating reagents, activated esters of peptides, etc. as described previously. The reagents in the mixtures to be added to the reaction vials are preferably present in equimolar concentrations and the total amount (moles) of the added reagents is two times the amount (moles) of 2-deoxystreptamine in the reaction vial. This is necessary if the 2-deoxystreptamine is to be functionalized on both of the amino groups. Therefore, $\frac{2}{3}$'s (two-thirds) of an equivalent (relative to the number of moles of 2-deoxystreptamine) of each reagent will be added to each reaction. A smaller amount of reagents may be used if it is desired that one of the amine groups not be functionalized. The ten different mixtures of reagents preferably include thirty different reactive species (i.e., three reagents per mixture with each mixture containing different reagents from the other mixtures). The reagents should be (to the extent possible) grouped according to their expected reactivity toward the amine groups of 2-deoxystreptamine so that all of the constituents of the product mixtures will be present in equivalent amounts. To the reaction mixtures are added any additional reagents required for coupling to occur (such as dicyclohexylcarbodiimide (DCC) in the case of a peptide coupling). After the reactions are complete, they are halted by the addition of a solvent that preferably precipitates the products while leaving reagents and any by-products in solution. The vials are then placed in a centrifuge and the product precipitate pelleted. The supernatant is then removed from the reaction vials, and the pellet resuspended in the precipitation solvent with the aid of a vortex mixer. The resultant suspension is again treated to centrifugation, and the solvent decanted. This washing procedure is performed three times and the samples so obtained are then dried in vacuo. The relative amounts of the products of the mixtures can be ascertained by standard high performance chromatographic methods.

The compound library can be subjected to biological assay. Mixtures exhibiting the desired properties can be deconvoluted to determine the identity of the active constituent. Deconvolution can be performed directly by high performance chromatographic means (using bioactivity guided fractionation), or "deconvolution libraries" can be generated where the reagent mixtures used to functionalize the 2-deoxystreptamine scaffold are reduced to either one, or all possible combinations of two, of the three reagents that provided the original mixture that elicited a biological response. Mixtures prepared in this manner will indicate by their comparative bioactivity profiles which functionality (ies) are responsible for the observed effect.

Preparation of Combinatorial Libraries of O- and for N-Functionalized 2-Deoxystreptamine.

The following procedure describes the preparation of a combinatorial library containing molecules based on the 2-deoxystreptamine scaffold that are functionalized on the hydroxyl groups of the parent scaffold. As mentioned above, the chemistry used to functionalize the hydroxyl groups will often require that the amine groups of 2-deoxystreptamine be protected. Standard protecting groups, as well as the groups listed specifically above, can be employed for this purpose. Also, if libraries containing substituents on both the amino groups and the hydroxyl groups of 2-deoxystreptamine are desired, the amino groups can be functionalized first with the resultant products being exposed to the following procedure, or unprotected 2-deoxystreptamine can be used directly in the following procedure with the knowledge that the amine groups be preferentially functionalized first due to their greater nucleophilicity. This procedure will prepare 270 different chemical entities as 10 mixtures containing 27 compounds per mixture. Into each of an array of 10 vials is placed a quantity of the appropriately N-protected-2-deoxystreptamine in a solvent. The amount of the 2-deoxystreptamine based starting material used per vial is defined by the final amount required of each chemical entity to be prepared in that vial (if 2 µmoles of each compound is required for biological assay then the 2-deoxystreptamine moiety must be used at 27 times that amount per vial). The solvent to be used should preferably be both organic- and water-soluble, such as THF, DMF, or DMSO. The nature of the appended groups will dictate the method of compound isolation. To the array of 10 vials that contain the N-protected-2-deoxystreptamine, at an appropriate temperature (preferably 0° C.) are added sequentially 10 different mixtures of the reagents to be appended to the 2-deoxystreptamine scaffold. These mixtures will contain preferably three different reagents. The reagents may be acyl halides, acyl anhydrides, etc., as described previously. The reagents in the mixtures to be added to the reaction vials are preferably present in equimolar concentrations and the total amount (moles) of the added reagents preferably is 3 times the amount of N-protected-2-deoxystreptamine in the reaction vial. This is necessary if the 2-deoxystreptamine is to be functionalized on all three of the hydroxyl groups. A smaller amount of reagents is used if it is desired that one or more of the hydroxyl groups not be functionalized. Therefore, one equivalent (relative to the number of moles of 2-deoxystreptamine) of each reagent will be added to each reaction. The ten different mixtures of reagents preferably include thirty different reactive species (i.e., three reagents per mixture with each mixture containing different reagents from the other mixtures). The reagents should be (to the extent possible) grouped according to their expected reactivity toward the hydroxyl groups of N-protected-2-deoxystreptamine so that all of the constituents of the product mixtures will be present in equivalent amounts. To the reaction mixtures are added any additional reagents required for coupling to occur (such as triethylamine, pyridine, dimethylaminopyridine (DMAP), or diisopropylethylamine). After the reactions are complete, they are halted by the addition of a solvent that preferably precipitates the formed products while leaving reagents and any by-products in solution. The vials are then placed in a centrifuge and the product isolated, as described in Example 1. At this point any chemistry that is required for the deprotection of the amine groups of the 2-deoxystreptamine can be performed, followed by a similar precipitation, centrifugation, washing procedure as described above. The relative amounts of the constituents of the mixtures can be ascertained by standard high performance chromatographic methods.

The compound library can be subjected to biological assay, with mixtures exhibiting the desired properties being deconvoluted to determine the identity of the active constituent. Deconvolution can be performed or "deconvolution libraries" can be generated where the reagent mixtures used to functionalize the N-protected-2-deoxystreptamine scaffold are reduced to either one, or all possible combinations of two, of the three reagents that gave the original mixture that elicited a biological response. Mixtures prepared in this manner will indicate by their comparative bioactivity profiles which functionality are responsible for the observed effect.

2-DOS Functionalized Chromatographic Supports

Into a chromatography column suitable for doing standard biological chromatography is placed a pre-activated commercially available solid support that has been pretreated (swollen, washed, etc.) with appropriate solvents (buffers, eluents) according to the manufacturer's protocol. The amount of the resin to be used is dependent on the relative concentration of the activated functionality present on the resin and the desired amount of 2-deoxystreptamine or modified 2-deoxy-streptamine ligand desired to be incorporated onto the support. The column support is chosen such that the reactive functionality of the support is appropriate for covalent bond formation with the desired functionality of the 2-deoxystreptamine derived material as (such as cyanogen bromide activated agarose for amine groups as described above etc.). The packed column is then charged with a solution of the 2-deoxystreptamine derived ligand in a solvent and along with the reagents necessary for the coupling reaction to occur (usually a slightly basic, non-denaturing, non-amine containing buffer such as 0.1 M $NaHCO_3$ buffer, pH 8.3). The solution thus charged is then allowed to elute into the column support material and is kept there for a specific time and at a suitable temperature as required by the manufacturer. After the coupling reaction is complete the remaining reactive functional groups on the column support that have not reacted with a 2-deoxystreptamine ligand are blocked. This is accomplished by washing the column with a suitable blocking agent (such as, for example, aqueous solutions of ethanolamine, or glycine). The column is then washed free of excess 2-deoxystreptamine ligand and blocking reagent with an eluent appropriate for the separation experiment to be performed. Columns prepared in this manner are routinely stored 4° C.

Synthesis of Combinatorial Libraries of Aminoglycoside Mimics Based on 2-Deoxystreptamine Targeting the Transcriptional REV-RRE Interaction of Human Immunodeficiency Virus.

The aminoglycosides are a clinically useful class of antibiotics that are used both topically and internally to combat a broad array of bacterial infections. Unfortunately, the aminoglycoside antibiotics exhibit high cytotoxicity, inadequate bioavailability, and are becoming ineffective due to the development of resistant organisms resulting from their ubiquitous use. Clearly, a new generation of antibiotics is required that address these deficiencies; however, the preparation of large numbers of analogs of these synthetically inaccessible molecules using a traditional medicinal chemistry approach was not feasible.

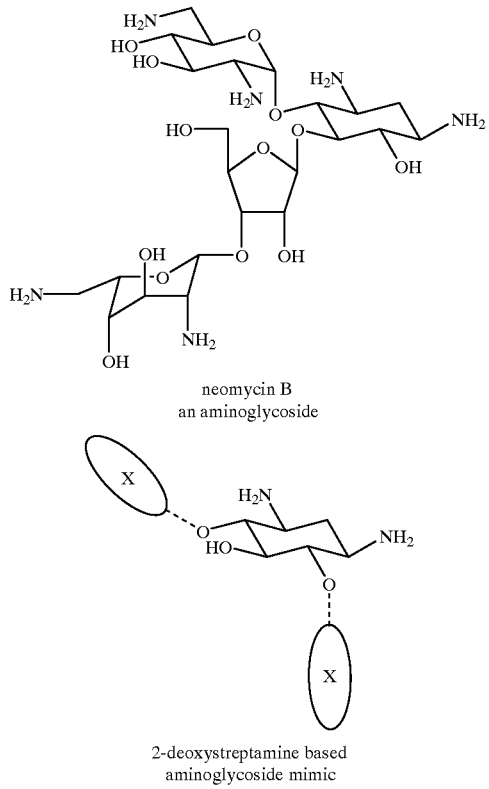

neomycin B
an aminoglycoside 2-deoxystreptamine based
aminoglycoside mimic

The combinatorial preparation of aminoglycoside antibiotic analogs based on 2-deoxystreptamine is an example of directed molecular diversity generation where what is known about the SAR of the parent molecule is incorporated into the planning of the specific libraries to be generated. The 1 and 3 position amines of the 2-deoxystreptamine ring system in the parent aminoglycoside series is thought to be important for biological function. Therefore, the libraries that were generated intentionally did not include functionality on these amines.

Treatment of 2-deoxystreptamine, prepared from neomycin B, with 2,5-hexanedione afforded the dimethylpyrrole protected compound 2 shown in Scheme XVI in 65% yield. This compound served as a branchpoint between the random and regiochemically controlled synthetic schemes. The triol 2 can be alkylated directly to afford diversity (if multiple benzylic halides are used) or the material can be protected as the acetonide and used to prepare materials of known regiochemical substitution.

Scheme XVI

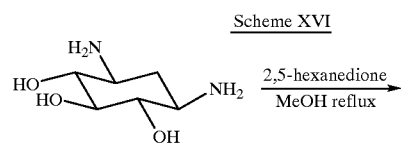

1

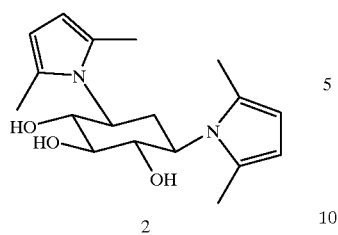

Compound 2 was allowed to react with 2,2-dimethoxypropane in acetone in the presence of a catalytic amount of p-toluenesulfonic acid to afford the racemic acetonide 3 in high yield. Lipschitz et al., *J. Org. Chem.* 1988, 53, 4495.

Scheme XVII

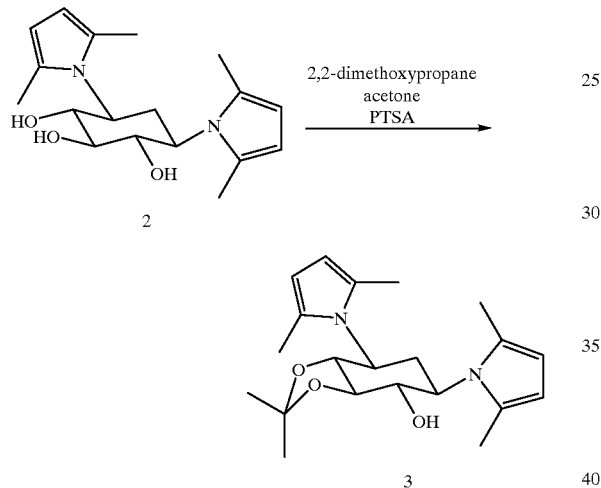

Triol 2 can be used directly to generate precursors for molecular diversity generation. Triol 2 was treated with excess sodium hydride in THF at reflux to generate the poly-alkoxide which was exposed to an excess of p-cyanobenzyl bromide to provide the tri-alkylated adduct 4 (see Scheme XVIII). This procedure can also be performed with either o, or m, cyanobenzyl bromide. The cyano groups of the aromatic rings were used for diversity generation in a protocol that will be discussed subsequently.

Scheme XVIII

Triol 2 was also treated with sodium hydride in THF at reflux with two equivalents of p-cyanophenyl fluoride to afford di-substituted compounds such as 5 as mixtures of regiochemical isomers (see Scheme XIX).

Scheme XIX

Triol 6, prepared using standard methods, was treated to isopropylisocyanate in pyridine at room temperature to afford a tri-(isopropylcarbamate)-di-N-benzyloxycarbonyl-2-deoxystreptamine derivative (7) that was subsequently deprotected under conditions of catalytic hydrogenation to afford compound 8 (see Scheme XX).

Scheme XX

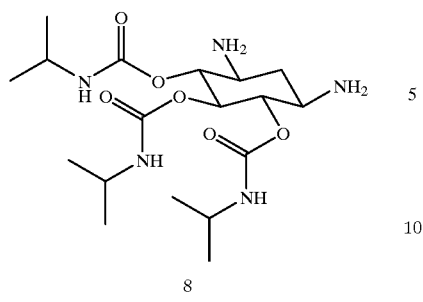

8

Methods for generation of combinatorial libraries where regiochemical control of the position of the pendant groups was desired were based on compound 3. The free hydroxyl of compound 3 was alkylated with pendant groups that would either serve as hydrogen bonding functionality, mimic the relative steric requirements of the parent neomycin B, or would serve as precursors for the creation of desired functionality. Compound 3 was alkylated with groups such as picolyl (either 2, 3, or 4 Compound 9b 3-picolyl is shown), m-nitrobenzyl, or cyanophenyl as can be seen in Scheme XXI.

Scheme XXI

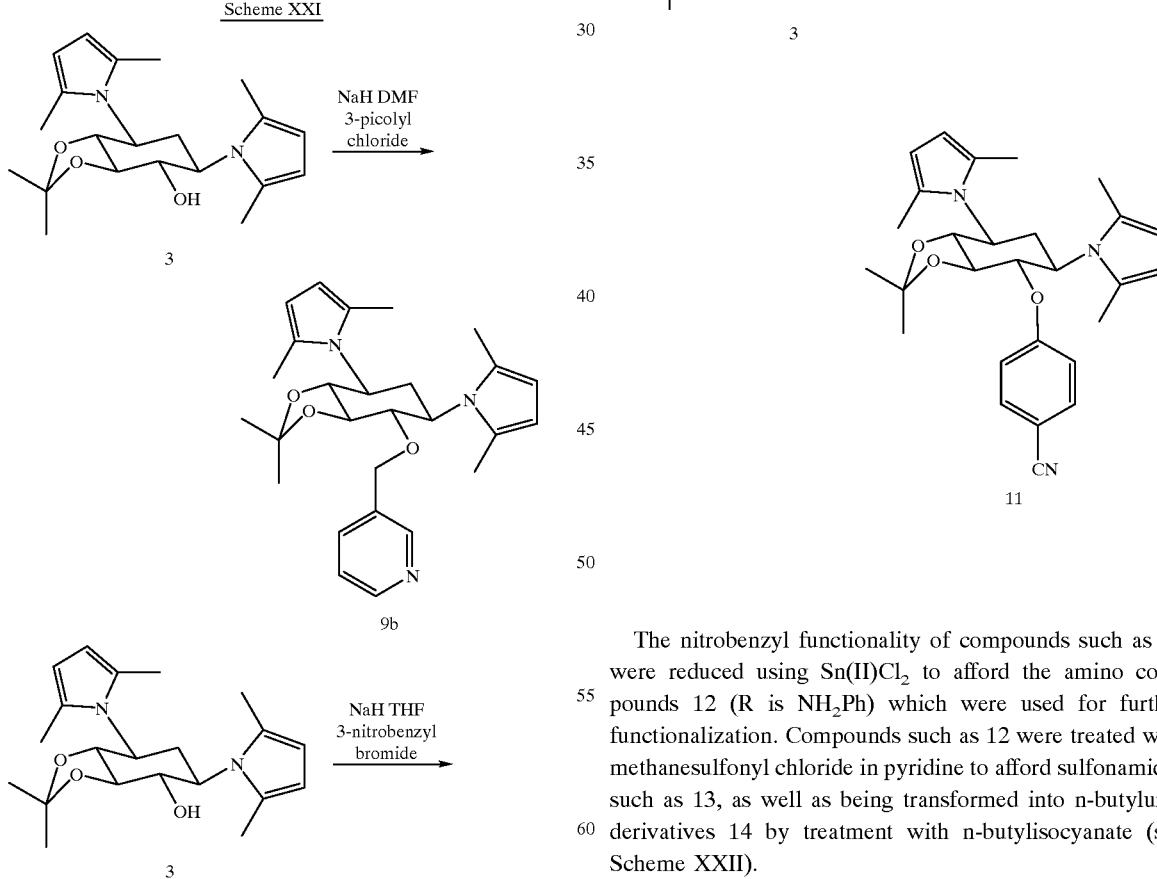

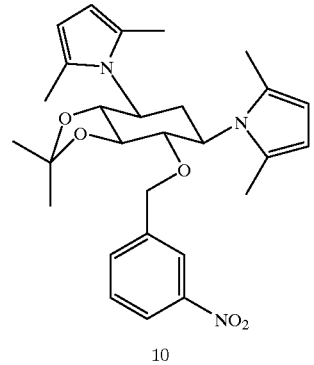

The nitrobenzyl functionality of compounds such as 10 were reduced using Sn(II)Cl$_2$ to afford the amino compounds 12 (R is NH$_2$Ph) which were used for further functionalization. Compounds such as 12 were treated with methanesulfonyl chloride in pyridine to afford sulfonamides such as 13, as well as being transformed into n-butylurea derivatives 14 by treatment with n-butylisocyanate (see Scheme XXII).

Scheme XXII

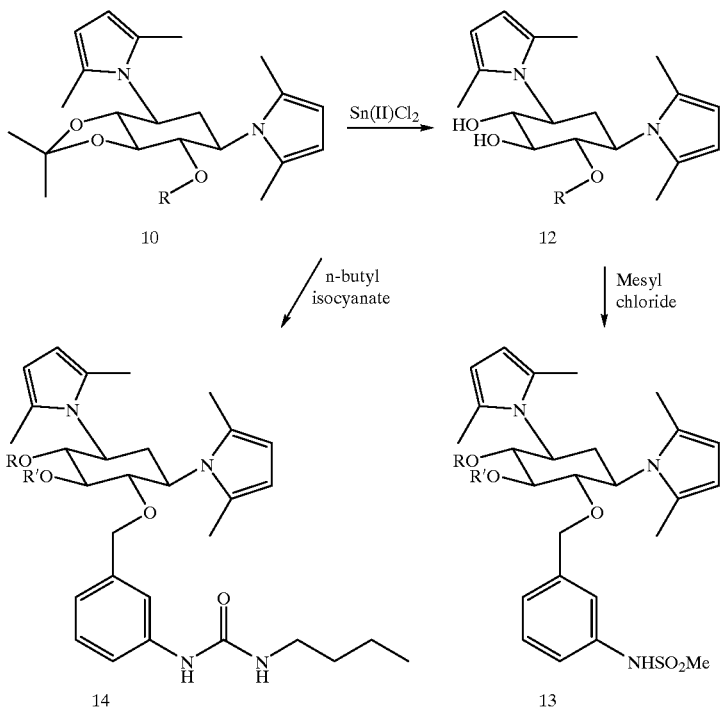

The acetonide functionality of the various analogs was found to be conveniently removed by treatment with Sn(II) Cl₂ in an ethyl acetate/methanol mixture to afford diols such as 15 and 16, a, b, c (see scheme XXIII).

Scheme XXIII

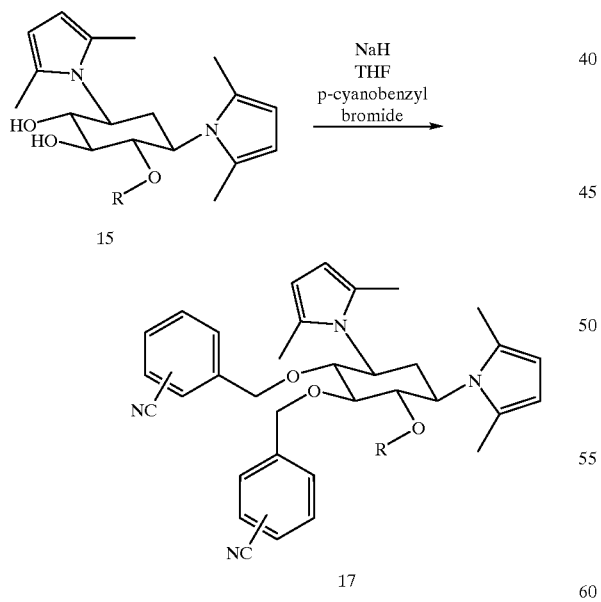

Diols 15 and 16, a, b, c were then treated with excess sodium hydride in THF at reflux to generate the bis-alkoxide which was exposed to an excess of o- or, m- or, p-cyanobenzyl bromide to provide adducts such as 17 and 18 a, b, c, d (see scheme XXIV). This procedure can also be performed with either o, or m, cyanobenzyl bromide.

Scheme XXIV

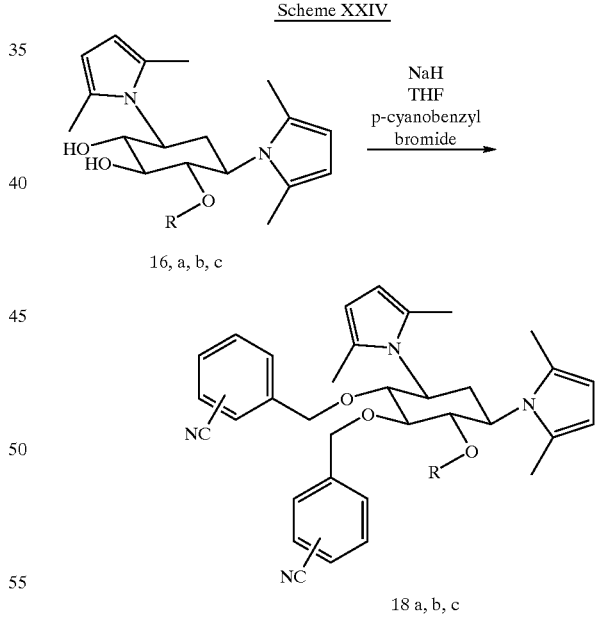

Generation of libraries of compounds designed to bind to RNA based on 2-deoxystreptamine was performed using all of the pure materials described above containing pendant cyano-aryl functionalities. Molecular diversity was generated by employing the known transformation of an aryl-cyano group into an aryl-imidate by exposing the cyano compound to HCl gas in an anhydrous alcohol solvent (preferably ethanol). This transformation is shown in Scheme XXV below.

Scheme XXV

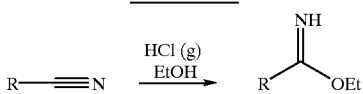

These conditions also remove the dimethyl pyrrole protecting group, freeing the protected amine which is isolated as the HCl salt. Because the amines of the 2-deoxystreptamine are isolated in their protonated form, there is no danger of their reacting with the imidate functionality. Treatment of the imidate with mixtures of amines affords large numbers of arylamidine-substituted 2-deoxystreptamine derivatives.

Figure 1B:
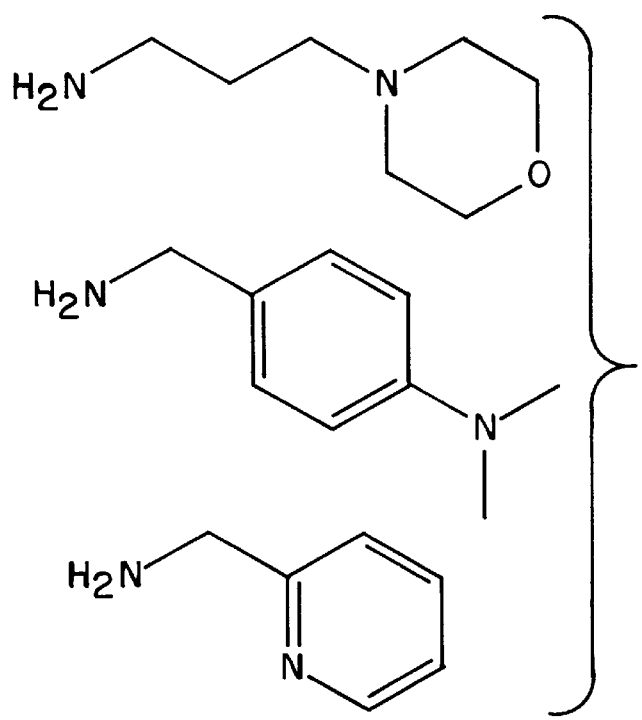
Figure 2A:
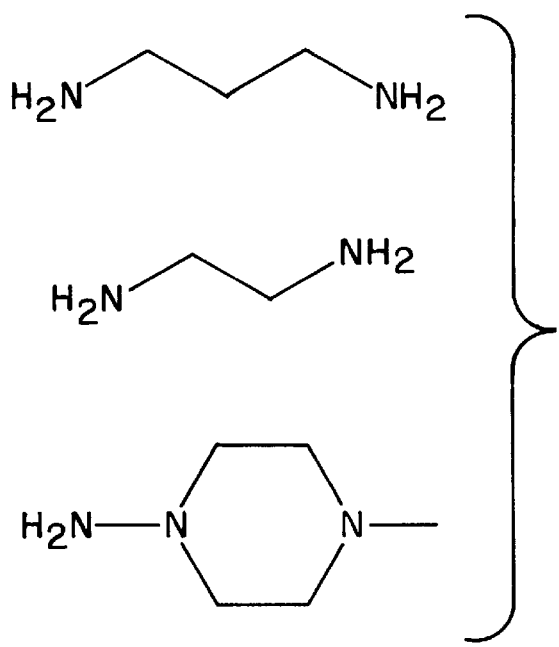
Figure 2B:
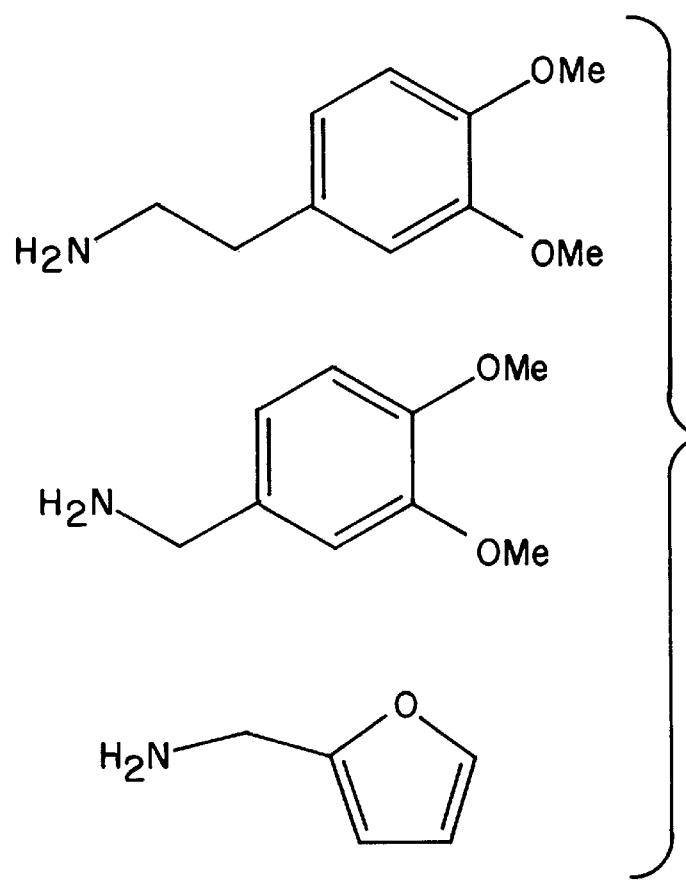
Figure 3A:
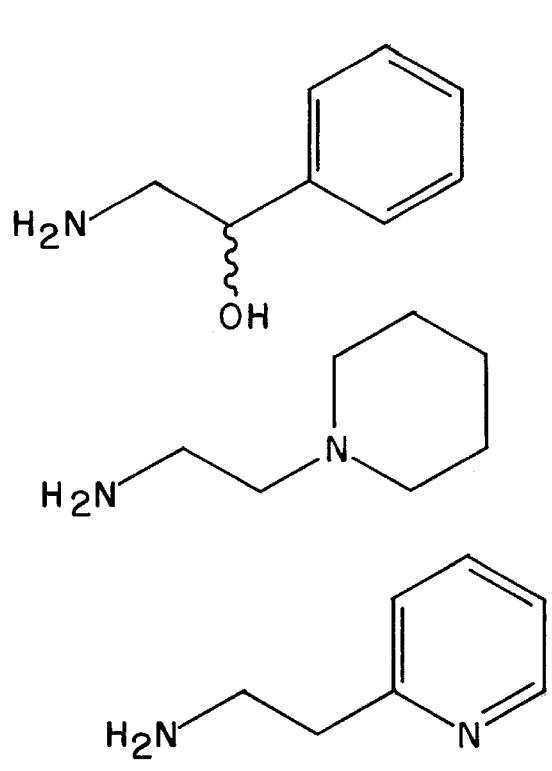
Figure 3B:
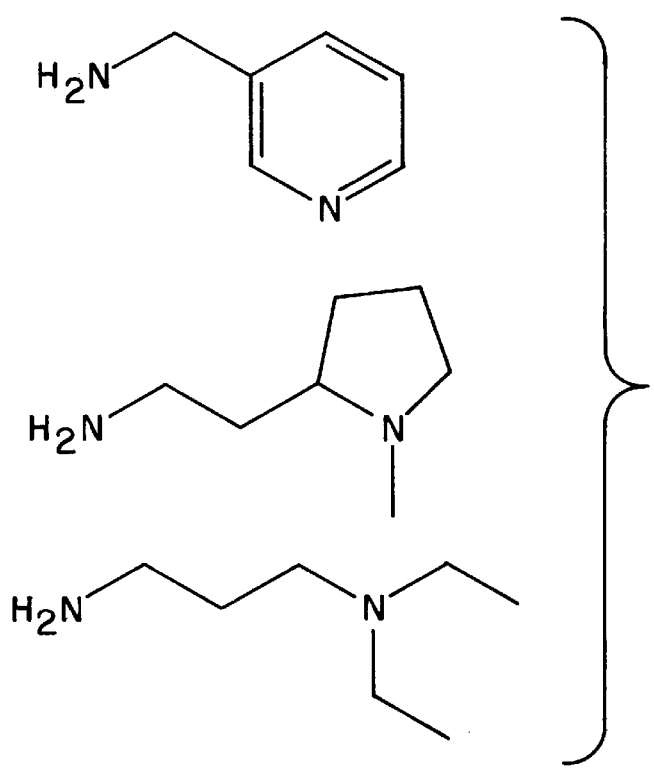
Figure 4A:
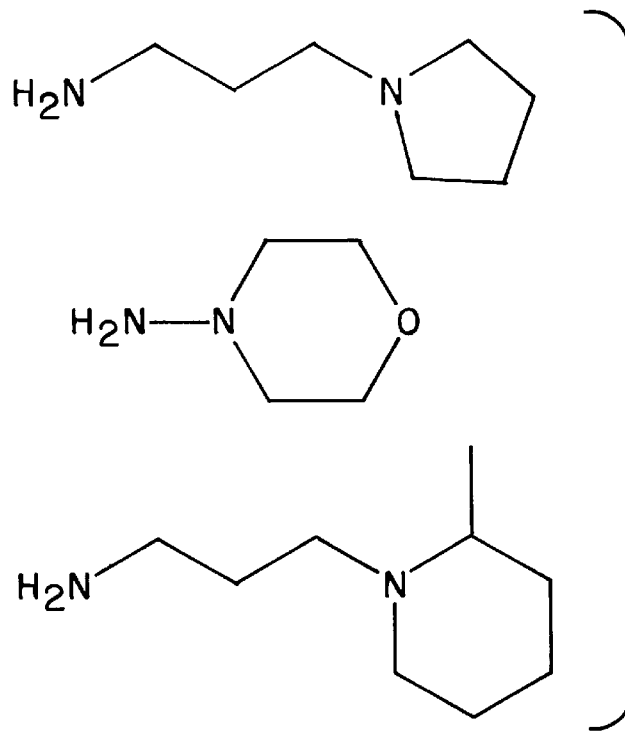
Figure 4B:
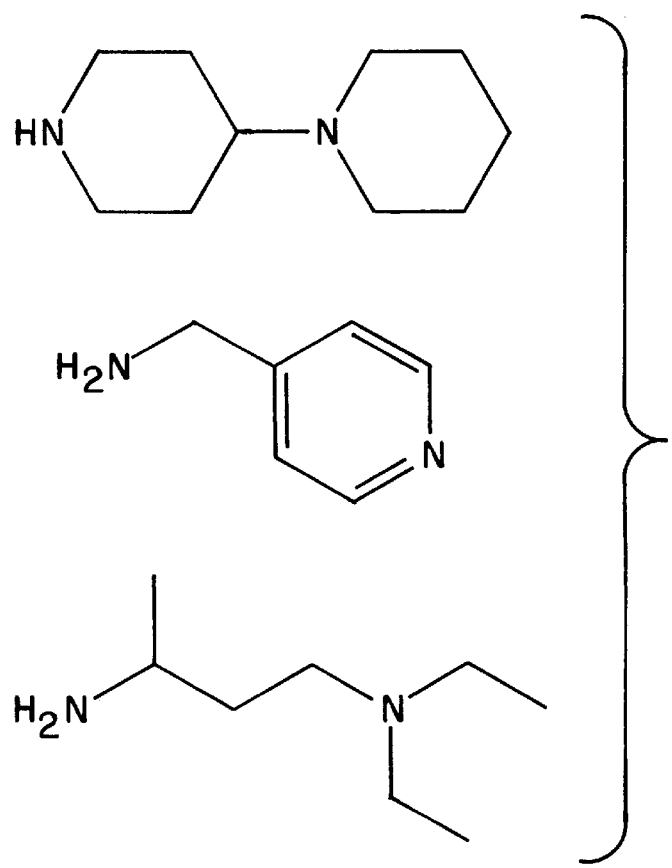
Figure 5A:
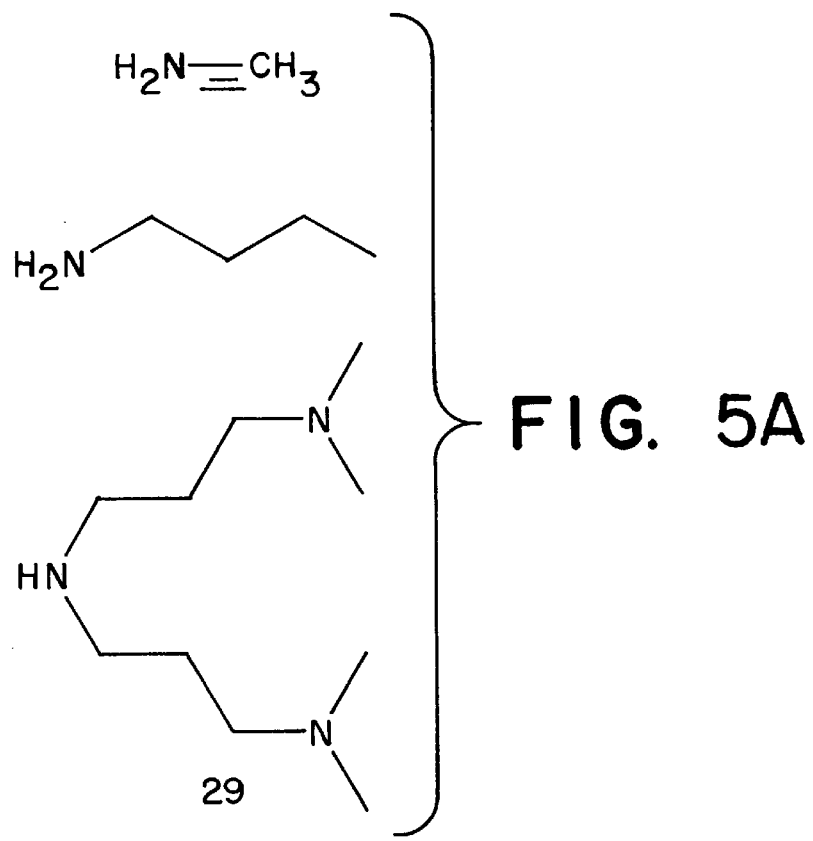
Figure 5B:
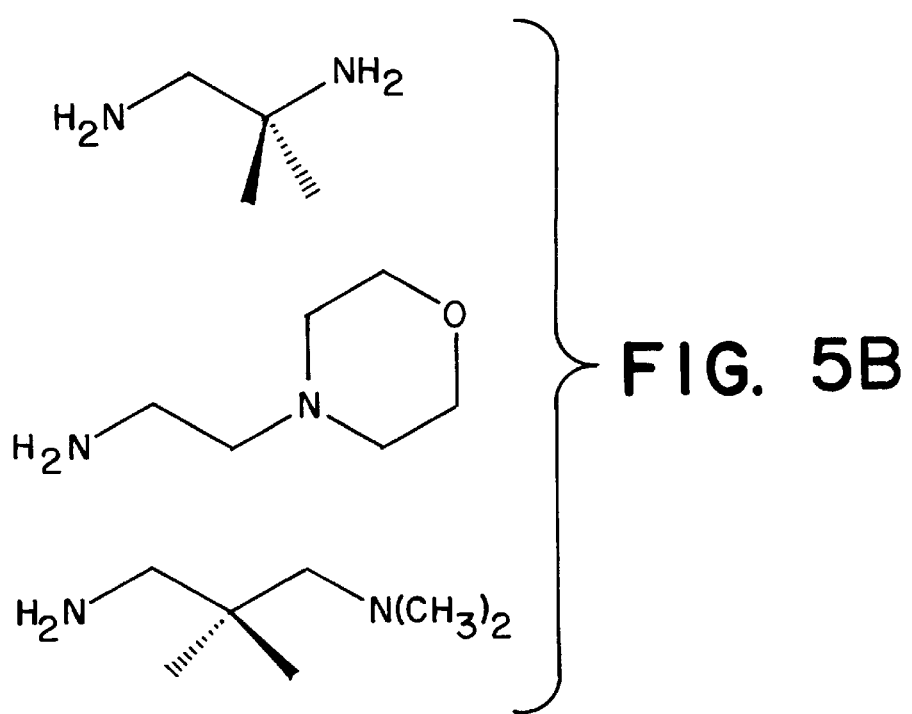
Figure 6A:
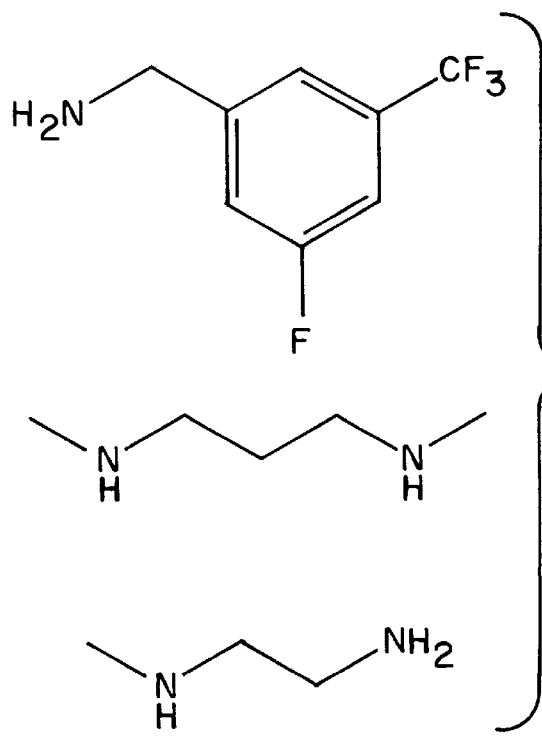
Figure 6B:
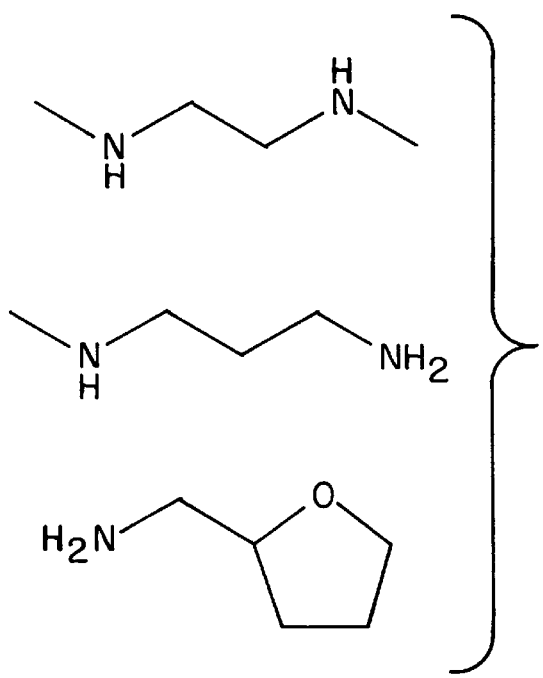

The arylamidine chemistry and functionality were chosen for several reasons. Large numbers of amines are commercially available. The chemistry is very dependable and proceeds in high yield. Most primary amines will exhibit roughly the same reactivity toward the intermediate imidate and therefore all possible compounds to be formed will be present in the mixtures in equivalent amounts. The amidine functionality is protonated at physiological pH, and by virtue of being so, will enhance the affinity of the compounds for the poly-anionic RNA The amines that were chosen to be used in the diversity generating reaction mixtures are shown in their appropriate groupings in FIGS. 1A–6B. The procedure for library generation is described in example 19 below.

Utilities

The compounds taught above containing a 2-DOS substructure are useful to inhibit HIV REV/RRE binding interaction in vivo and in vitro. The ability of these compounds to inhibit the binding of HIV REV protein to HIV RRE indicates that the compounds are useful to treat, prevent or ameliorate human immunodeficiency viral disease.

In addition, the combinatorial library methods disclosed herein are generally useful to identify compounds with various biological activities. Accordingly, using these methods, compounds with anticancer, antiviral, antifungal or antibacterial activities, inter alia, may be identified. Such combinatorial libraries constructed in accord with the present methods are assayed by routine methods known in the art to identify those compounds with the highest activity.

The magnitude of the prophylactic or therapeutic dose of the compounds of the invention will vary with the nature and severity of the condition to be treated and with the particular compound and its route of administration. In general, the daily dose range for anti-HIV activity lies in the range of 0.001 to 25 mg/kg of body weight in a mammal, preferably 0.001 to 10 mg/kg, and most preferably 0.001 to 1.0 mg/kg, in single or multiple doses. In unusual cases, it may be necessary to administer doses above 25 mg/kg.

Any suitable route of administration may be employed for providing a mammal, especially a human, with an effective dosage of a compound disclosed herein. For example, oral, rectal, topical, parenteral, ocular, pulmonary, nasal, etc., routes may be employed. Dosage forms include tablets, troches, dispersions, suspensions, solutions, capsules, creams, ointments, aerosols, etc.

The pharmaceutical compositions of the present invention comprise a compound containing a 2-DOS substructure disclosed herein, or a pharmaceutically acceptable salt thereof, as an active ingredient, and may also contain a pharmaceutically acceptable carrier and, optionally, other therapeutically active ingredients.

The compositions include compositions suitable for oral, rectal, topical (including transdermal devices, aerosols, creams, ointments, lotions and dusting powders), parenteral (including subcutaneous, intramuscular and intravenous), ocular (ophthalmic), pulmonary (nasal or buccal inhalation) or nasal administration. Although the most suitable route in any given case will depend largely on the nature and severity of the condition being treated and on the nature of the active ingredient. They may be conveniently presented in unit dosage form and prepared by any of the methods well known in the art of pharmacy.

In preparing oral dosage forms, any of the unusual pharmaceutical media may be used, such as water, glycols, oils, alcohols, flavoring agents, preservatives, coloring agents, and the like in the case of oral liquid preparations (e.g., suspensions, elixers and solutions); or carriers such as starches, sugars, microcrystalline cellulose, diluents, granulating agents, lubricants, binders, disintegrating agents, etc., in the case of oral solid preparations are preferred over liquid oral preparations such as powders, capsules and tablets. If desired, capsules may be coated by standard aqueous or non-aqueous techniques. In addition to the dosage forms described above, the compounds of the invention may be administered by controlled release means and devices.

Pharmaceutical compositions of the present invention suitable for oral administration may be prepared as discrete units such as capsules, cachets or tablets each containing a predetermined amount of the active ingredient in powder or granular form or as a solution or suspension in an aqueous or nonaqueous liquid or in an oil-in-water or water-in-oil emulsion. Such compositions may be prepared by any of the methods known in the art of pharmacy. In general compositions are prepared by uniformly and intimately admixing the active ingredient with liquid carriers, finely divided solid carriers, or both and then, if necessary, shaping the product into the desired form. For example, a tablet may be prepared by compression or molding, optionally with one or more accessory ingredients. Compressed tablets may be prepared by compressing in a suitable machine the active ingredient in a free-flowing form such as powder or granule optionally mixed with a binder, lubricant, inert diluent or surface active or dispersing agent. Molded tablets may be made by molding in a suitable machine, a mixture of the powdered compound moistened with an inert liquid diluent.

Description of the Preferred Embodiments

The following examples are illustrative of the invention but are not intended to limit the scope of the invention.

EXAMPLE 1

Preparation 2-Deoxystreptamine (2-DOS)

To a 1 L round bottom flask equipped with a condenser was added neomycin sulfate (27.2 g, 0.03 mol) and HBr (48%, 300 mL). The solution was heated at reflux for 20 hrs. Upon cooling to room temperature, the black solution was concentrated to dryness under reduced pressure. $H_2O$ (100 mL) was then added to the black solid, and after vigorous stirring, the slurry was filtered and the filtrate was lyophilized. The dark brown solid obtained was washed with 150 mL of 1:2:1 $CHCl_3$:MeOH:$NH_3$ (con.) and the residue was stirred in 450 mL of hot 1:1 14 O:MeOH solution to dissolve most of the material. This solution was filtered and the filtrate was allowed to stand at room temperature overnight. The water:methanol mixture was filtered again and the filtrate was lyophilized. The light brown solid obtained was washed with 100 mL of 1:1 EtOH:$H_2O$ to remove $NH_4Br$. The remaining solid (ca. 9 g) was dissolved in minimal $H_2O$ and was purified by passing over Amberlite 440C ion-exchange resin (OH— form, 90 g). The fractions were assayed with ninhydrin. This afforded 2.36 g (48%) of white 2-DOS free base. TLC $R_f$ 0.41 (1:4:2:1 $CHCl_3$:MeOH:$NH_3$ (con.):$H_2O$); mp 212° C. (dec.);

¹H NMR (D₂O): d 1.15 (q, 1H), 1.95 (m, 1H), 2.68 (m, 2H), 3.12 (t, 2H), 3.25 (t, 1H).
¹³C NMR (D₂O): d 36.0, 50.6, 75.8, 77.9.
Ref: J. Carbohydrate Chemistry, 10(5), 739–748, 1991

EXAMPLE 2

In a dry round bottom flask was placed 2,5 hexanedione (22.6 g, 15.8 ml, 198 mmol) and 1 (5.4 g, 33 mmol) in 200 ml of MeOH. The mixture, which became a pale yellow homogenous solution after 0.5 hrs of heating at reflux, was heated at reflux in the dark overnight. The solution was then cooled to 0° C. and was kept at that temperature for 4 hours. The first crop of white crystalline product (3.8 g) was collected by filtration and was washed with MeOH at −70° C. An additional 3.0 g of the crystalline product was collected by filtration after the filtrate had been refrigerated (at about 10° C.) overnight; yield: 65%.

¹H NMR (d₆-MeOH): d 1.85 (m, 1H), 2.22 (s, 6H), 2.38 (s, 6H), 2.70 (q, 1H), 3.37 (t, 1H), 4.05 (m, 2H), 5.66 (dd, 2H).

EXAMPLE 3

In a dry round bottom flask was placed 2 (4.0 g, 12.56 mmol) and p-toluenesulfonic acid (48 mg, 0.251 mmol, 2 mol %) in 300 ml of dry dimethoxypropane. To this solution was added 200 ml of dry acetone via cannulation. The solution was stirred in the dark at room temperature overnight. 200 ml of aqueous NH₄Cl was added to quench the reaction. The solvent was removed under reduced pressure to one-third of its original volume and was extracted in a separatory funnel with CHCl₃ twice. The organic layer was dried (Na₂SO₄) and concentrated with the aid of a rotary evaporator to an orange solid. Recrystallization of the solid in ethyl acetate yielded 3.1 g of the desired product, which was used in subsequent reactions without further purification yield 69%.

¹H NMR (CDCl₃): d 1.49 (s, 6H), 2.14 (m, 1H), 2.25 (s, 3H), 2.26 (s, 3H), 2.41 (s, 6H), 2.63 (q, 1H), 3.62 (t, 1H), 4.26 (m, 2H), 5.79 (m, 2H).

EXAMPLE 4

To a flame-dried flask under flushing argon containing 0.19 g (0,43 mmole, 1 eq) 2, stirring in 20 ml of freshly distilled THF was added 0.031 g (1.29 mmol,) of NaH as a 60% mineral oil dispersion. Upon the cessation of effervescence, 0.092 g (0.47 mmol) of p-cyanobenzylbromide was added to the flask. The reaction was lowered into an oil bath and heated to reflux. The reaction was heated for 5 hrs. The excess NaH was quenched by the addition of 1N NH₄Cl. The THF was removed with the aid of a rotary evaporator. The residue was placed on a SiO₂ column and eluted with 20% ethyl acetate/hexanes. This provided 57.6 mg of white waxy solid (20%). Also 56.9 mg (24%) of 5, the dialkylated isomers were isolated.

¹H NMR (300 MHz, CDCl₃): d 7.61 (d, 2H), 7.49 (d, 4H), 7.32 (d, 2H), 7.04 (d, 4H), 5.80 (m, 4H), 4.89 (s, 2H), 4.20 (d, 2H), 4.13 (m, 2H), 3.89 (t, 2H), 3.75 (d, 2H), 3.55 (t, 1H), 3.12 (q, 1H), 2.43 (s, 6H), 2.25 (s, 6H) ppm.

EXAMPLE 5

To a flame-dried flask under flushing argon containing 0.2 g (630 μmole, 1 eq) 2, stirring in 20 ml of freshly distilled THF was added 75 mg (1.9 mmole, 3 eq) of NaH as a 60% mineral oil dispersion. Upon the cessation of effervescence, 0.23 g (1.9 mmol, 3 eq) of p-cyanophenylfluoride was added to the flask. The reaction was lowered into an oil bath and heated to reflux. The reaction was heated for 16 hrs. The color of the solution was opaque brown. The excess NaH was quenched by the addition of 1 N NH₄Cl. The THF was removed on a rotary evaporator. The reaction was diluted with CH₂Cl₂. The organic solution was washed in a separatory funnel with saturated NaHCO₃ and brine. The organic layer was dried with Na₂SO₄, filtered and concentrated with the aid of a rotary evaporator. The residue was placed on a SiO₂ column and eluted with 40% ethyl acetate/hexanes. This afforded 3 mg of a yellow oil (1%) that was about 80% pure (mixture of regioisomers) by NMR.

¹H NMR (300 MHz, CDCl₃): d 2.30 (12H, s); 2.40 (1H, dt); 3.20 (1H, quart); 4.40 (2H, m); 4.85 (3H, m); 5.65 (2H, d); 6.60, 6.95, 7.40, 7.50 (8H, all d).

EXAMPLE 6

To a round bottom flask containing 20 mL of 200 mM aqeous K₂CO₃ was added 2-deoxystreptamine (free amine) (327 mg, 2.02 mmol) with stirring. To the room temperature solution was added benzyloxycarbonyl chloride (0.64 mL, 4.23 mmol) and the resultant solution stirred for 30 min. The white sold that formed was filtered and dried in vaccuo to afford 430 mg (1.49 mmol, 74% yield) of the desired product that was used without further purification.

¹H NMR (d₆-DMSO) δ=7.38 (m, 10H), 7.09 (d, 2H), 5.01 (s, 4H), 3.22 (m, 10 2H), 3.02 (m, 3H), 1.82 (ddd, 1H), 1.21 (ddd, 1H) ppm.

EXAMPLE 7

To a flame-dried flask under flushing argon containing 50 mg (120 μmole, 1 eq) of di-N-benzyloxycarbamate (Cbz), protected 2-DOS, stirring in 1 ml of freshly distilled pyridine was added 57 μl (580 μmol, 5 eq) of isopropylisocyanate. The reaction was stirred for 24 hours until no starting material was present by TLC. The reaction was stopped by dilution with 15 ml of chloroform and extraction of the solution sequentially with 1% HCl, saturated NaHCO₃, and brine solution. The organic layer was dried with Na₂SO₄, filtered and evaporated on a rotary evaporator. The residue was placed on a SiO₂ column and eluted with 10% methanol/CHCl₃. This yielded 43 mg of a white solid (54%).

¹H NMR (300 MHz, d₄-methanol): d 1.00 (18H, m); 1.45 (1H, quart); 2.05 (1H, dt); 3.20–3.80 (5H, m); 4.50 4.80 (3H, m); 5.05 (2H, s); 5.10 (2H, s); 7.30 (10H, m).

EXAMPLE 8

In a Parr shaker bottle was placed 42 mg (61 μmol) of 7 in 4 ml of a 1:1 mixture of ethyl acetate and methanol, 10 mg of 10% palladium on carbon and 1 drop of acetic acid. The flask was placed on a Parr hydrogenation apparatus and the atmosphere of the reaction vessel flushed 3 times with hydrogen gas. The reaction was placed under 50 psi of H₂ and the flask shaken for 24 hours. The reaction mixture was filtered though Celite and the solvent evaporated with the aid of a rotary evaporator. This yielded 23 mg of a yellow oil (>96%) that was used without further purification. ¹H NMR (300 MHz, d₄-methanol): d 1.10 (18H, m); 1.60 (1H, quart); 2.30 (1H, dt); 3.20–3.80 (5H, m); 4.50 4.90 (3H, t).

Examples 9 a, b, c

NaH (60% dispersion in mineral oil, 3.3 g, 83.7 mmol) was added to a dry 150 ml DMF solution of 3 (3.0 g, 8.37 mmol) and was heated to 60° C. in the dark for 1 hour.

2-picolyl chloride (2.82 g, 17.2 mmol) was added in 4 portions over a period of 15 minutes. After heating the reaction mixture at 60° C. for another hour, the solution was poured onto ice. The aqueous layer was extracted with $CHCl_3$ three times and the resultant organic layer was extracted twice with dilute $NaHCO_3$ solution. The combined organic layers were then dried with $Na_2SO_4$, filtered, and concentrated under reduced pressure. The crude product was chromatographed ($SiO2$ 1:1:1 hexanes: $EtOAc:CHCl_3$). 3.2 g of product 9a was collected.

Following the same procedure compounds 9b and 9c were prepared.

9a: $^1H$ NMR ($CDCl_3$): d 1.48 (s, 6H), 2.27 (s, 3H), 2.28 (s, 3H), 2.30 (s, 3H), 2.39 (s, 3H), 2.70 (q, 1H), 3.68 (t, 1H), 4.20 (m, 2H), 4.58 (q, 2H), 5.77 (m, 2H), 6.86 (d, 1H), 7.11 (m, 1H), 7.54 (m, 1H), 8.46 (d, 1H); yield: 85%.

9b: $^1H$ NMR ($CDCl_3$): spectral data similar to 3a, aromatic region: d 7.17 (m, 1H), 7.29 (m, 1H), 8.33 (s, 1H), 8.49 (d, 1H), yield: 80%.

9c: $^1H$ NMR ($CDCl_3$): spectral data similar to 3a, aromatic region: d 6.82 (d, 2H), 8.35 (d, 2H); yield: 53%.

EXAMPLE 10

To a flame-dried flask under flushing argon containing 1.0 g (2.8 mmole, 1 eq) of 2-DOS, protected as its dipyrroloacetonide, stirring in 40 ml of freshly distilled THF was added 0.279 g (7.0 mmol, 2.5 eq) of NaH as a 60% mineral oil dispersion. Upon the subsiding of the effervescence, 0.724 g (3.3 mmol, 1.2 eq) of 3-nitrobenzylbromide was added to the flask. The reaction was lowered into an oil bath and heated to reflux. The reaction was heated for 1.5 hrs until no starting material was present by TLC. The color of the solution is opaque brown. The excess NaH was eliminated by the addition of 1 N $NH_4Cl$. The THF was removed on a rotary evaporator. The reaction was diluted with $CH_2Cl_2$. The solution was extracted with saturated $NaHCO_3$ and brine. The organic layer was dried with $Na_2SO_4$, filtered and evaporated on a rotary evaporator. The residue was placed on a $SiO_2$ column and eluted with 25% ethyl acetate/hexanes. This yielded 1.9 g of a white solid (89%).

$^1H$ NMR (300 MHz, $CDCl_3$): d 1.45 (3H, s); 1.50 (3H, s); 2.20 (1H, dt); 2.25 (12H, s); 2.70 (1H, quart); 3.65 (1H, t); 4.00 (1H, t); 4.104.30 (3H, m); 4.40 (2H, dd); 5.75 (2H, s); 5.80 (2H, s); 7.30 (1H, d); 7.40 (1H, t); 8.05 (1H, s); 8.10 (1H d).

EXAMPLE 11

To a flame-dried flask under flushing argon containing 25 mg (44 µmole, 1 eq) 3, stirring in 2 ml of freshly distilled THF was added 5 mg (130 µmol, 3 eq) of NaH as a 60% mineral oil dispersion. Upon the subsiding of the effervescence, 10 mg (88 µmol, 2 eq) of p-cyanophenylfluoride was added to the flask. The reaction was lowered into an oil bath and heated to reflux. The reaction was heated for 5 hrs . The color of the solution is opaque brown. The excess NaH was eliminated by the addition of 1 N $NH_4Cl$. The THF was removed on a rotary evaporator. The reaction was diluted with $CH_2Cl_2$. The solution was extracted with saturated $NaHCO_3$ and brine. The organic layer was dried with $Na_2SO_4$, filtered and evaporated on a rotary evaporator. The residue was placed on a $SiO_2$ column and eluted with 33% ethyl acetate/hexanes. This yielded 2 mg of a yellow oil (7%).

$^1H$ NMR (300 MHz, $CDCl_3$): d 2.20 (6H, s); 2.25 (6H, s); 2.30 (1H, dt); 2.45 (6H, s); 3.15 (1H, quart); 3.75 (2H, m); 4.00 (4H, m); 4.15 (2H, m); 4.45 (1H, m); 5.80 (2H, m); 6.80 (2H, d); 7.00 (1H, d); 7.10 (2H, d); 7.30 (1H, t); 7.45 (2H, d); 7.65 (2H, d); 7.70 (1H, s); 8.1 (1H d).

EXAMPLE 12

To a flask containing 0.195 g (0.29 mmole, 1 eq) of 10, stirring in 15 ml of a 1:1 mixture of ethyl acetatelmethanol was added 0.322 g (1.4 mmol, 5 eq) of $SnCl_2·2H_2O$. The reaction was heated at reflux for 16 hrs until no starting material was present by TLC. The reaction was stopped by dilution with 25 ml of ethyl acetate and the subsequent addition of saturated $NaHCO_3$ solution. This resulted in the formation of a precipitate. The reaction mixture was placed in Falcon tubes and centrifuged for 5 min. The supernatant was decanted and the aqueous and organic layers were separated. Both the solid and the aqueous layer were extracted twice with ethyl acetate. All the organic layers were combined and extracted once with brine solution. The organic layer was dried with $Na_2SO_4$, filtered and evaporated on a rotary evaporator. The residue was placed on a $SiO_2$ column and eluted with 33% hexanes/ethyl acetate. This yielded 0.135 g of a yellow oil (73%).

$^1H$ NMR (300 MHz, $CDCl_3$): d 2.20 (1H, dt); 2.25 (3H, s); 2.30 (3H, s); 2.40 (3H, s); 2.45 (3H, s); 3.10 (1H, quart); 3.50 (1H, t); 3.75 (2H, m); 3.90 (2H, m); 4.10 (3H, m); 4.20 (1H, d); 4.90 (2H, dd); 5.80 (4H, m); 6.20 (1H, s); 6.40 (1H, d); 6.55 (1H, d); 7.00 (1H, t) 7.05 (2H, d); 7.30 (2H, d); 7.50 (2H, d); 7.60 (2H, d).

EXAMPLE 13

To a flame-dried flask under flushing argon containing 28 mg (43 µmole, 1 eq) of 12, stirring in 2 ml of freshly distilled pyridine was added 7 µl (86 µmol, 2 eq) of methanesulfonyl chloride by syringe. The reaction became an orange/yellow and was stirred for 30 minutes at room temperature. Another equivalent of methanesulfonyl chloride was added by syringe. After 1 hour, no starting material was present by TLC and the solution was a light pink. The reaction was stopped by dilution with 15 ml of chloroform and extraction of the solution sequentially with 1% HCl, saturated $NaHCO_3$ and brine solution. The organic layer was dried with $Na_2SO_4$, filtered and concentrated on a rotary evaporator. The residue was placed on a $SiO_2$ column and eluted with 30% ethyl acetate/hexanes. This yielded 30 mg of a white solid (96%).

$^1H$ NMR (300 MHz, $CDCl_3$): d 2.20 (1H, dt); 2.25 (3H, s); 2.30 (3H, s); 2.40 (3H, s); 2.45 (3H, s); 3.10 (1H, quart); 3.50 (1H, t); 3.75 (2H, m); 3.90 (2H, m); 4.10 (4H, 5 m); 4.90 (2H, dd); 5.80 (4H, m); 6.75 (1H, d); 6.85 (1H, s); 7.05 (2H, d); 7.15 (2H, m); 7.30 (2H, d); 7.45 (2H, d); 7.55 (2H, d).

EXAMPLE 14

To a flame-dried flask under flushing argon containing 68 mg (104 µmole, 10 1 eq) of 12, stirring in 2 ml of freshly distilled pyridine was added 12.3 µl (109 µmol, 1.05 eq) of n-butyl isocyanate by syringe. The reaction was stirred for 16 hours at room temperature. Another equivalent of n-butyl isocyanate was added by syringe. After an additional 4 hours, no starting material was present by TLC. The reaction was stopped by dilution with 15 ml of chloroform and extraction of the solution sequentially with 1% HCl, saturated $NaHCO_3$ and brine solution. The organic layer was dried with $Na_2SO_4$, filtered and evaporated on a rotary evaporator. This yielded 70 mg of a glassy solid (89%). This product was used without further purification.

$^1$H NMR (300 MHz, CDCl$_3$): d 0.90 (3H, t); 1.30 (2H, m); 1.45,(2H, m); 2.20 (1H, dt); 2.25 (3H, s); 2.30 (3H, s); 2.40 (6H, s); 3.10 (1H, quart); 3.20 (2H, t); 3.50 (1H, t); 3.75 (2H, m); 3.90 (2H, m); 4.15 (4H, m); 4.90 (2H, dd); 5.80 (4H, m); 6.65 (1H, d); 6.75 (1H, s); 7.05 (4H, m); 7.30 (2H, d); 7.45 (2H, d); 7.55 (2H, d).

EXAMPLE 15

To a flask containing 1.2 g (2.4 mmole, 1 eq) of 10 stirring in 100 ml of ethyl acetate was added 2.74 g (12.0 mmol, 5 eq) of SnCl$_2$—2H$_2$O. The reaction was stirred for 2 hrs until no starting material was present by TLC. The reaction was stopped by the addition of saturated NaHCO$_3$ solution. This resulted in the formation of a precipitate. The reaction mixture was placed in Falcon tubes and centrifuged for 5 min. The supernatant was decanted and the aqueous and organic layers were separated. Both the solid and the aqueous layer were extracted twice with ethyl acetate. The organic layers were combined and extracted once with brine solution. The organic layer was dried with Na$_2$SO$_4$, filtered and evaporated on a rotary evaporator. The residue was placed on a SiO$_2$ column and eluted with 40% hexanes/ethyl acetate. This yielded 0.96 g of a white solid (90%).

$^1$H NMR (300 MHz, CDCl$_3$): d 2.20 (1H, dt); 2.25 (6H, s); 2.40 (6H, s); 2.95 (1H, quart); 3.60 (1H, t); 3.80 (1H, t); 3.90 (1H, d);4.004.20 (3H, m); 4.30 (1H, d); 5.75 (2H, s); 5.80 (2H, s); 7.30 (1H, d); 7.40 (1H, t); 8.05 (1H, s); 8.10 (1H, d).

EXAMPLE 16 a, b, c

In a dry round bottom flask were placed SnCl$_2$.2H$_2$O (0.55 g, 2.43 mmol), 9a (1.10 g, 2.38 mmol) and MeOH (300 mL), and the solution was heated to 60° C. in the dark for 16 hours. After the reaction, 100 ml of saturated NaHCO$_3$ solution was added to the reaction mixture. The reaction mixture was then extracted with CHCl$_3$ three times. The combined organic layers were collected and filtered. The filtrate was dried with Na$_2$SO$_4$ and was concentrated under reduced pressure. Chromatography (SiO2, 20:1 CHCl$_3$:MeOH) afforded 0.82 g of product.

Following the same procedure compounds 16b and 16c were prepared.

16a: $^1$H NMR (CDCl$_3$): the spectrum is similar to that of 9a; absent the acetonide group methyl resonances. yield: 82%.

16b: $^1$H NMR (CDCl$_3$): the spectrum is similar to that of 9b; absent the acetonide group methyl resonances. yield: 73%.

16c: $^1$H NMR (CDCl$_3$): the spectrum is similar to that of 9c; absent the acetonide group methyl resonances. yield: 50%.

EXAMPLE 17

To a flame-dried flask under flushing argon containing 0.96 g (2.1 mmole, 1 eq) 15, stirring in 50 ml of freshly distilled THF was added 0.36 g (8.9 mmol, 4.2 eq) of NaH as a 60% mineral oil dispersion. Upon the subsiding of the effervescence, 0.87 g (4.4 mmol, 2.1 eq) of 3-nitrobenzylbromide was added to the flask. The reaction was lowered into an oil bath and heated to reflux. The reaction was heated for 5 hrs. The color of the solution is opaque brown. The excess NaH was eliminated by the addition of 1 N NH$_4$Cl. The THF was removed on a rotary evaporator. The reaction was diluted with CH$_2$Cl$_2$. The solution was extracted with saturated NaHCO$_3$ and brine. The organic layer was dried with Na$_2$SO$_4$, filtered and evaporated on a rotary evaporator. The residue was placed on a SiO$_2$ column and eluted with 30% ethyl acetate/ hexanes. This yielded 75 mg of a yellow oil (5%). Also, a mixture of the monoalkylated isomers, 0.272 g (19%), was isolated.

$^1$H NMR (300 MHz, CDCl$_3$): d 2.20 (1H, dt); 2.25 (6H, s); 2.40 (6H, s); 3.15 (1H, quart); 3.60 (1H, t); 3.75 (2H, m); 3.90 (2H, t); 4.15 (4H, m); 4.80 (2H, s); 5.75 (2H, s); 5.80 (2H, s); 7.05 (2H, d); 7.20 (2H, d); 7.30 (2H, d); 7.50 (2H, d); 7.55 (1H, d);7.60 (1H, t); 7.90 (1H, s); 8.1 (1H d).

EXAMPLE 18 a, b, c, d

To a dry round bottom flask was added 16a (300 mg, 0.71 mmol) in 50 ml of THF. NaH (60% dispersion in mineral oil, 285 mg, 7.12 mmol) was added to the solution. The reaction mixture was heated at reflux for 1 hour. p-cyanobenzyl bromide (558 mg, 2.85 mmol) was then added to the reaction in one portion. The reaction was monitored by TLC (1:1 hexanes:EtOAc). Water was added to quench the reaction upon completion. The aqueous layer was extracted with CHCl$_3$ three times. The combined organic layers were collected, dried with Na$_2$SO$_4$, filtered, and concentrated under reduced pressure. The crude material was chromatographed (SiO2, 4.5:3:2 hexanes:EtOAc:CHCl$_3$).

18a: R$_1$=2-picolyl, R$_2$=3-cyanobenzyl;
18b: R$_1$=2-picolyl, R$_2$=4-cyanobenzyl;
18c: R$_1$=3-picolyl, R$_2$=3-cyanobenzyl;
18d: R$_1$=4-picolyl, R$_2$=4-cyanobenzyl 18a: $^1$H NMR (CDCl$_3$): d 3.95 (2H), 4.84 (2H), aromatic region: 7.01–7.57 m, 11H), 8.45 (d, 1H); yield: 32%.

18b: $^1$H NMR (CDCl$_3$): d 3.97 (2H), 4.87 (2H), aromatic region: 6.97–7.15 (m, 4H), 7.32 (d, 2H), 7.50 (m, 5H), 8.44 (d, 1H); yield: 90%.

18c: $^1$H NMR (CDCl$_3$): differences between the $^1$H NMR spectra of 16b and 18c: d 3.62–4.20 (m, 6H), 4.82 (q, 2H), aromatic region: 7.09–7.58 (m, 1 OH), 8.25 (s, 1H), 8.48 (d, 1H); yield: 11%.

18d: $^1$H NMR (CDCl$_3$): d 2.20 (s, 3H), 2.21 (s, 3H), 2.42 (m, 1H), 2.43 (s, 6H), 3.13 (q, 1H), 3.5–4.23 (m, 7H), 4.87 (s, 2H), 5.80 (m, 2H), 6.89 (m, 2H), 7.14 (m, 2H), 7.29 (d, 2H), 7.48 (d, 2H), 7.58 (d, 2H), 8.43 (d, 2H); yield: 47%.

EXAMPLE 19

Experimental procedure for the synthesis of a combinatorial library of aminoglycoside mimics based on 2-deoxystreptamine. Analogs specifically intended to target the transcriptional rev-RRE interaction of the Human Immunodefficiency Virus.

The following procedure describes the preparation of a combinatorial library containing molecules that are based on the cyanobenzyl or cyanophenyl containing 2-deoxystreptamine scaffolds that are described above. All of the above compounds have been exposed to this protocol, to generate arrays of compounds. The procedure for the preparation of a library from compound 18b will serve as the illustrative example. This procedure will furnish 90 different chemical entities as 10 mixtures containing 9 compounds per mixture.

Preparation of the imidate.

Into a dry round bottom flask equipped with a magnetic stirbar is placed 18b (100 mg, 0.153 mmol) in anhydrous ethanol (10 mL) at 0° C. Into this stirred solution was bubbled dry HCl gas until the solution became saturated (usually 3–5 min.). The reaction is allowed to stir for 30 minutes as it slowly warms to room temperature. TLC of the solution ($SiO_2$, 1:1 ethyl acetate: hexanes) indicated absence of starting material, and formation of a new UV active baseline spot. The solution was concentrated to dryness with the aid of a rotary evaporator and then dried in vacuo.

Preparation of amidines.

Into each of an array of 10 vials is placed 14 μL of a 2 M solution of amines in anhydrous ethanol. The amine mixtures used are A through J as described above and A–J correspond to vials 1 through 10 accordingly. The amine concentration of the mixtures in total is 2 M with each of the three amines in the mixture being present as 0.66 M. Into each of the 10 vials is placed ethanol (0.5 mL) and diisopropylethyl amine (24 μL). To the 10 stirred reaction vessels at room temperature is added 500 μL of a 5 mL solution containing 0.14 mmol of the imidate formed from compound 18b in anhydrous ethanol. The reactions are stirred at room temperature overnight to ensure completion and then the products are precipitated out of solution by the addition of $Et_2O$ (10 mL). The reagents remain in solution. The reactions are then placed in a centrifuge and the product precipitate pelleted. The supernatant is then removed from the reaction vials, and the pellet resuspended in the precipitation solvent with the aid of a vortex mixer. The resultant suspension is again treated to centrifugation, and the solvent decanted. This washing procedure is performed three times and the samples so obtained are then dried in vacuo. The relative amounts of the constituents of the mixtures can be ascertained by standard high performance chromatographic methods. The library so prepared is ready to be subjected to biological assay, with mixtures exhibiting the desired properties being deconvoluted to determine the identity of the active constituent. Deconvolution can be performed directly by high performance chromatographic means (using bioactivity guided fractionation), or "deconvolution libraries" can be generated where the reagent mixtures used to functionalize the 2-deoxystreptamine scaffold are reduced to either one, or all possible combinations of two, of the three reagents that gave the original mixture that elicited a biological response. Mixtures prepared in this manner will indicate by their comparative bioactivity profiles which functionality are responsible for the observed effect. The procedure for the preparation of the "deconvolution libraries" is exactly parallel to the procedure described above except for the mentioned difference of the number of amines used in reaction mixtures.

EXAMPLE 20 INHIBITION OF BINDING OF REV TO RRE

Following the procedure in Example 19, the following compounds were prepared and tested for binding of HIV Rev protein in the HIV RRE.

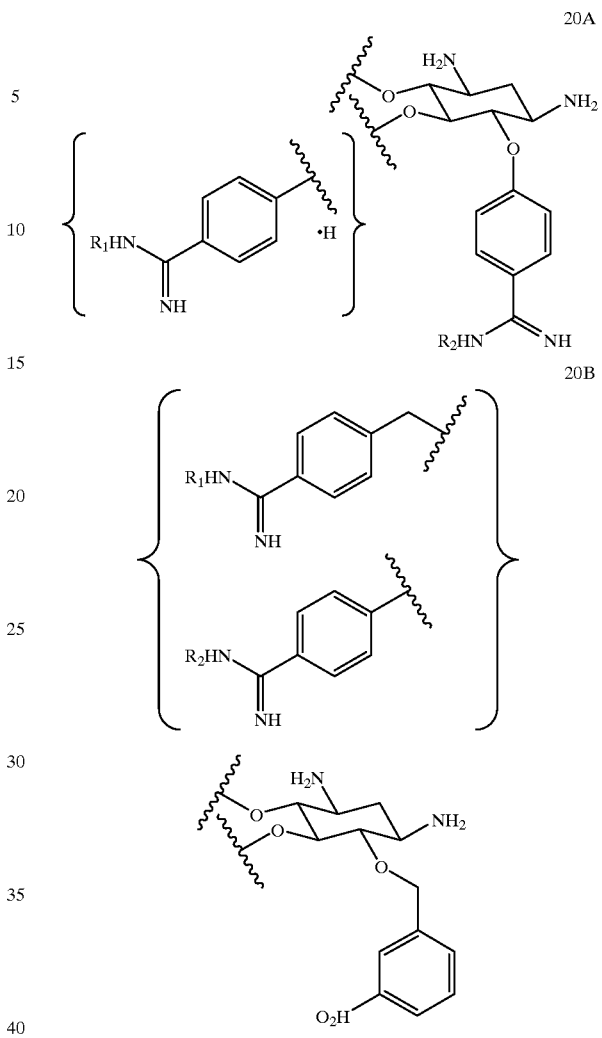

The following experiment was performed to test the inhibition by test compounds of the binding of HIV Rev protein to the HIV RRE.

A 69-nt $^{32}$P-labelled RNA probe containing a high affinity Rev-binding site (Bartel et al., *Cell* 67:529, 1991) was incubated with purified *E. coli*-derived Rev protein in the absence and presence of increasing concentrations of Compound 7a. Reactions conditions were those that maximize the specificity of the interaction between Rev and the RRE, i.e., 150 mM KCl and a 100-fold molar excess of tRNA.

After a 30-minute incubation at room temperature, a nitrocellulose filter-binding assay was performed to quantify the binding of Rev to the RRE (Daly et al., *Biochem.* 32:10497, 1993). In this assay, RNA is retained on the filter only by virtue of binding to Rev. Filter-associated radioactivity was quantified in a Wallac Microbeta counter. The fraction of input RNA retained on the filter was plotted as a function of Compound concentration, and the $IC_{50}$ (the concentration required to inhibit 50% Rev-RRE binding) was determined by linear regression.

The results shown in Table 1 indicate that the compounds of the invention inhibit Rev-RRE interaction in a concentration-dependent fashion.

TABLE 1

| Compound | IC$_{50}$ | | |
| --- | --- | --- | --- |
| | R$_1$ and R$_2$ 3-dimethyl- aminopropyl | R$_1$ and R$_2$ 3-diethyl- aminopropyl | R1 and R2 3-(2-methylpiper- idino)propyl |
| 20A | 8.7 μM | 9.2 μM | 12.4 μpM |
| 20B | 12 μM | 18.4 μM | >100 μM |

EXAMPLE 21
Preparation of Allyl Carbamate 2-DOS

A buffer was made by dissolving HEPES (Na salt) (10.4 g; 40 mmol) and calcium chloride dihydrate (510 mg; 4 mmol) in water (50 mL). The pH was adjusted to 7.8 with conc. HCl and the volume was brought up to 100 mL. The buffer is 400 mM HEPES with 40 mM calcium chloride. 2-Deoxystreptamine (100 mg; 0.616 mmol) was dissolved in 6 mL of the HEPES buffer and diluted with 6 mL of DMF. This affords a solution that is 200 mM in HEPES and 20 mM in calcium chloride. The reaction is performed in a Falcon tube to keep the enzyme from adhering to a glass surface. The reaction was treated with 350 mg diallyl carbonate (2.4 mmol) and subtilisin BPN (20 mg). The reaction was allowed to proceed for 7 days with 3 more additions of diallyl carbonate (3×350 mg; 2.4 mmol). The reaction was filtered and the filtrate concentrated in vacuo. The ion exchange chromatographic method described in B. Orsat et al., *J.Amer. Chem. Soc.* 1996, 118, 712, as modified herein, was used to purify the product.

The solids remaining after concentration were dissolved in 5 mL of water. 5 g of Amberlite IRC-50 weakly acidic ion exchange resin was swolled in water. The resin was then converted into its ammonium form by stirring with 10% ammonium hydroxide for 20 min. The resin was then washed repeatedly with water until the wash decantations were neutral to pH paper. The resin was placed in a column (1.5×9 cm) and a needle affixed to the end of the column to control the flow rate (ca. 1 mL/min). 2.5 mL of the solution were loaded onto the column which was then eluted as follows: (1) 5 mL fractions were collected; (2) 25 mL of water was allowed to elute "pre-gradient"; (3) at fraction 6, a linear gradient began from 0 to 3% ammonium hydroxide (fractions 6–45). After the fractions were collected, 1 λ of each fraction was spotted on a TLC plate and the plate was developed with p-anisaldehyde as visualizing agent. Fractions 19–24 were found to contain the expected product whose structure was confirmed by NMR. Optical rotation [α]$_D$ was plotted as a function of fraction number, and rises at fraction 18 (0.003), peaks at fraction 22 (0.020) and declines at fraction 25 (0.003).

For scale-up, a larger column (2×14 cm) is used with the same resin, and a flow rate of 1.2 mL/min, with fractions collected for 5 min. Elution of 25 mL water is followed by a linear gradient of 0 to 3% ammonium hydroxide. TLC of each fraction revealed that the product was in fractions 29–33. Upon lyophilization, the general procedure was the same as for the small scale work up, but the column and elution volume were larger to accomodate the larger amount of material.

EXAMPLE 22
Preparation of Bis-cyclic Carbamates of 2-DOS

Method A. To a solution of 2-DOS (2 g; 12.3 mmol) in 50 mL ice cold water was added sodium carbonate (1.6 g; 15.1 mmol) followed by p-nitrophenyl chloroformate (5.05 g; 27.3 mmol) in 80 mL acetone. The reaction mixture was stirred overnight during which time precipitate formed. 300 mg sodium bicarbonate was added and the mixture was again stirred overnight. The volume of the reaction mixture was reduced by evaporating the acetone. The precipitate formed was filtered and washed with water. The solid was recrystallized from methanol/water (1:1), affording 728.7 mg of the desired product.

Method B. To an ice-cold mixture of 2-DOS in 1 mL aqueous solution and 3.5 mL of Dowex 1×2 (hydroxide form) was added 340 mg of p-nitrophenyl chloroformate in 3.4 mL of acetone over 3–5 minutes. Both solutions were kept at 0° C. After stirring for 60 minutes, another 3.5 mL of Dowex resin and 340 mg of p-nitrophenyl chloroformate in cold acetone was added. The solution became thick and difficult to stir. Four product spots were observed by TLC, developed with acetone/EtOAc (2:1). The reaction mixture was washed with 4×10 mL ether. DMF was removed, and 97 mg of a yellow solid was obtained. The solid was dissolved in DMF, and applied to a flash chromatography column to obtain 67 mg of the desired product.

EXAMPLE 23
Preparation of N,N-Bis-Argininyl 2-DOS

Step A. α,ε,ω-Tri(benzyloxycarbonyl) arginine, N-succinimidyl ester (1.24 mmol) was dissolved in dioxane/water (2:1; 30 mL). 2-DOS (100 mg; 0.62 mmol) was added in one portion as a solid. The reaction mixture was stired overnight. Water addition resulted in precipitation of product. After filtration, the solid was dried in vacuo, and then dissolved in DMSO and passed through an Amberlite IRC-50 column (weakly acidic ion exchange resin, acid form). The fractions containing product were pooled and the product was precipitated by addition of water. Product was collected by filtration and dried in vacuo, and used directly in the reduction step.

Step B. The product of step A was dissolved in DMF in a Parr bottle. Pd/C (10%) was added. The bottle was charged to 50 psi with hydrogen gas, and shaken for one day. The reaction mixture was filtered through Celite. Ether was added, resulting in product precipitation. 30 Mg of the solid N,N-bisargininyl 2-DOS was collected by filtration and dried in vacuo.

EXAMPLE 24
Preparation of Peracetylated Bis-Argininyl 2-DOS

N,N-Bis-argininyl 2-DOS (3.8 mg) was suspended in pyridine (2 mL) and acetic anhydride (2 mL) at room temperature. After stirring for two days, the reaction mixture became homogeneous. Standard work-up and purification afforded the peracetylated product.

EXAMPLE 25
Preparation of N-Aroyl Functionalized Libraries from 2-DOS

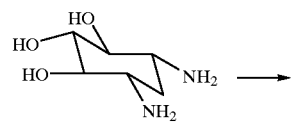

-continued

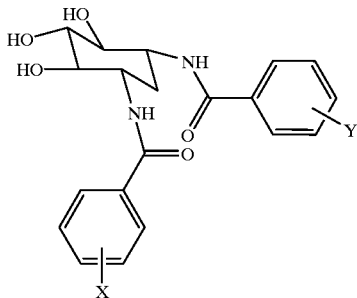

2-DOS (324 mg; 2 mmol) slurried in DMF at room temperature is reacted with 4/3 eq of the following aroyl chlorides: o-toluoyl chloride, m-toluoyl chloride, p-toluoyl chloride, 2-chlorobenzoyl chloride, 3-chlorobenzoyl chloride, 4-chlorobenzoyl chloride, o-anisoyl chloride, m-anisoyl chloride and p-anisoyl chloride (a total of 4 mmol).

EXAMPLE 26
Preparation of N,N-Bis-(p-Methoxybenzyl)-2-DOS

2-DOS (200 mg; 1.23 mmol), p-methoxybenzaldehyde (336 mg; 2.5 mmol) and sodium cyanoborohydride (155 mg; 2.5 mmol) were stirred in methanol at reflux temperature. Product was obtained after standard work-up and purification.

EXAMPLE 27
Preparation of N,N-Bis-(Cbz-Glycyl)-2-DOS

2-DOS (100 mg; 0.617 mmol), Cbz-Gly (258 mg; 1.23 mmol) were dissolved in THF and stirred at room temperature. EDAC-HCl (235.8 mg; 1.23 mmol) was added, and then diisopropylethylamine (216 µL; 1.23 mmol) was injected. The reaction mixture was stirred over 48 hours, and then concentrated. The residue was washed with water, pelleted and dried in vacuo, affording 65 mg of product.

EXAMPLE 28

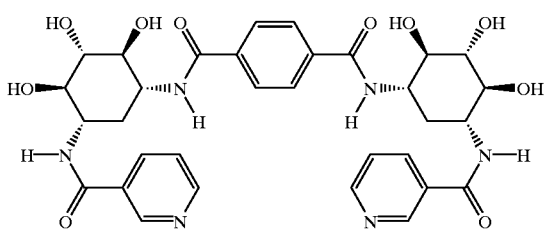

Amidation of Terephthaloyl chloride with N-mono (pyridylmethyl) 2-DOS (I)

2-DOS (162 mg; 1 mmol) in methanol was stirred at room temperature with potassium carbonate (760 mg; 5.5 mmol). Terephthaloyl chloride (101.5 mg; 0.5 mmol) was added. The reaction mixture was stirred for 0.5 hour, then nicotinyl chloride (178 mg; 1 mmol) was added. The reaction mixture was worked up using standard procedures, including flash chromatography, to provide 100 mg of product.

All patents, applications, test methods and publications mentioned herein are hereby incorporated by reference.

Many variations of the present invention will become apparent to those of skill in the art in light of the present disclosure. All such variations are within the intended scope of the appended claims.

What is claimed is:

1. A compound having the structure:

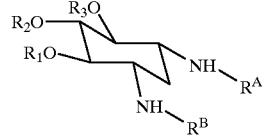

wherein $R^A$ and $R^B$ are independently hydrogen, alkyl, perfluoroalkyl, phenylmethyl, nitrophenylmethyl, (aminoimido)phenylmethyl, (alkylaminoimido) phenylmethyl, (acylaminoimido)phenylmethyl, acyl, aroyl, heteroaroyl, amino, alkylamino, arylamino, heteroarylamino, acylamino, aroylamino, heteroaroylamino, alkyloxycarbonylamino, aryloxycarbonylamino or heteroaryloxycarbonylamino; and wherein $R_1$ and $R_3$ are independently alkyl, aryl, heteroaryl, acyl, heteroaroyl or aroyl and $R_2$ is hydrogen.

2. The compound of claim 1 having the structure:

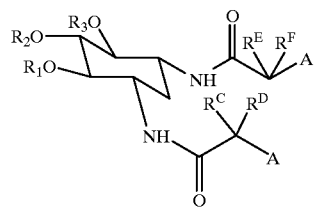

wherein A is hydrogen, alkyl, acyl, aroyl, heteroaroyl, amino, alkylamino, arylamino, heteroarylamino, acylamino, aroylamino, heteroaroylamino, alkyloxycarbonylamino, aryloxycarbonylamino or heteroaryloxycarbonylamino;

wherein $R^C$, $R^D$, $R^E$ and $R^F$ are independently hydrogen, alkyl, aryl, heteroaryl, arylalkyl, heteroarylalkyl, aminoalkyl, acylaminoalkyl, mercaptoalkyl or substituted or unsubstituted (aminoimido)aminoalkyl; and wherein $R_1$ and $R_3$ are independently alkyl, aryl or acyl and $R_2$ is hydrogen.

3. A compound having the structure:

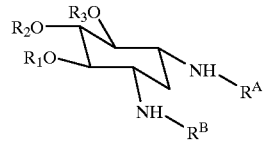

wherein $R^A$ and $R^B$ are independently hydrogen, alkyl, perfluoroalkyl, phenylmethyl, nitrophenylmethyl, (aminoimido)phenylmethyl, (alkylaminoimido) phenylmethyl, (acylaminoimido)phenylmethyl, acyl, aroyl, heteroaroyl, amino, alkylamino, arylamino, heteroarylamino, acylamino, aroylamino, heteroaroylamino, alkyloxycarbonylamino, aryloxycarbonylamino or heteroaryloxycarbonylamino; and wherein $R_3$ is hydrogen and $R_1$ and $R_2$ are selected from the group consisting of alkyl, aryl, heteroaryl, acyl, heteroaroyl and aroyl.

4. A compound having the structure:

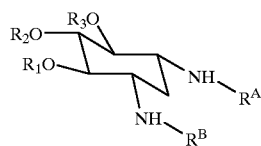

wherein $R^A$ and $R^B$ are independently hydrogen, alkyl, perfluoroalkyl, phenylmethyl, nitrophenylmethyl, (aminoimido)phenylmethyl, (alkylaminoimido)phenylmethyl, (acylaminoimido)phenylmethyl, acyl, aroyl, heteroaroyl, amino, alkylamino, arylamino, heteroarylamino, acylamino, aroylamino, heteroaroylamino, alkyloxycarbonylamino, aryloxycarbonylamino or heteroaryloxycarbonylamino; and wherein $R_1$ is hydrogen and $R_2$ and $R_3$ are selected from the group consisting of alkyl, aryl, heteroaryl, acyl, heteroaroyl and aroyl.

5. A pharmaceutical composition comprising a therapeutically effective amount of the compound of claim 1 and a pharmaceutically acceptable carrier.

6. A pharmaceutical composition for inhibiting binding of human immunodeficiency virus REV protein to RRE in cells comprising a therapeutically effective amount of the compound of claim 1 and a pharmaceutically acceptable carrier.

7. A method of inhibiting binding of human immunodeficiency virus REV protein to RRE in a subject comprising administering to the subject a therapeutically effective amount of the compound of claim 1.

8. A method of inhibiting binding of human immunodeficiency virus REV protein to RRE in cells comprising administering a therapeutically effective amount of the compound of claim 1.

* * * * *